US008951531B2

(12) United States Patent
Oloo et al.

(10) Patent No.: US 8,951,531 B2
(45) Date of Patent: Feb. 10, 2015

(54) **MODIFIED *STREPTOCOCCUS* PNEUMONIA PNEUMOLYSIN (PLY) POLYPEPTIDES**

(71) Applicant: The Kingdom of The Netherlands, Represented by The Minister of Health, Welfare and Sport, Bilthoven (NL)

(72) Inventors: Eliud Oloo, Toronto (CA); Raymond Oomen, Toronto (CA); Martina Ochs-Onolemhemhen, Lyons (FR); Jeremy Yethon, Toronto (CA)

(73) Assignee: The Kingdom of the Netherlands, Represented by the Minister of Health, Welfare and Sport, on Behalf of the Minister, The National Institute of Public Health and the Environment, Bilthoven (NL)

( * ) Notice: Subject to any disclaimer, the term of this patent is extended or adjusted under 35 U.S.C. 154(b) by 0 days.

(21) Appl. No.: 14/269,501

(22) Filed: May 5, 2014

(65) Prior Publication Data

US 2014/0341942 A1    Nov. 20, 2014

Related U.S. Application Data

(63) Continuation of application No. 13/140,894, filed as application No. PCT/CA2009/001843 on Dec. 22, 2009, now Pat. No. 8,758,766.

(60) Provisional application No. 61/140,804, filed on Dec. 24, 2008.

(51) Int. Cl.
| | | |
|---|---|---|
| A61K 39/00 | (2006.01) |
| A61K 39/02 | (2006.01) |
| A61K 39/09 | (2006.01) |
| A61K 39/38 | (2006.01) |
| C07K 14/315 | (2006.01) |
| C07K 16/12 | (2006.01) |

(52) U.S. Cl.
 CPC ......... *C07K 14/3156* (2013.01); *C07K 16/1275* (2013.01); *A61K 39/092* (2013.01); *C07K 2317/76* (2013.01)
 USPC .................. 424/190.1; 424/184.1; 424/185.1; 424/234.1; 424/235.1; 424/237.1; 424/278.1; 424/282.1; 435/91.1; 514/44

(58) Field of Classification Search
 None
 See application file for complete search history.

*Primary Examiner* — Ja'na Hines
(74) *Attorney, Agent, or Firm* — Patrick J. Halloran; Reza Yacoub

(57) ABSTRACT

This disclosure relates to modified *Streptococcus pneumonia* pneumolysm (PLY) proteins which lack hemolytic activity and can be used as immunogens in an immunogenic composition or vaccine against invasive pneumococcol diseases caused by *S. pneumonia* The modified pneumolysm proteins comprise amino acid substitutions at threonine 65, glycine 293 and cysteine 428 Nucleic acids, polypeptides encoded thereby, compositions containing the same, methods for using such nucleic acids, polypeptides and compositions are also provided.

14 Claims, 5 Drawing Sheets

*Exemplary "wtPLY" Amino Acid Sequences*
*Alleles and Modifications*

```
WT MANKAVNDFILAMNYDKKKLLTHQGESIENRFIKEGNQLPDEFVVIERKKRSLSTNTSD
M          D

WT ISVTATNDSRLYPGALLVVDETLLENNPTLLAVDRAPMTYSIDLPGLASSDSFLQVEDP

WT SNSSVRGAVNDLLAKWHQDYGQVNNVPARMQYEKITAHSMEQLKVKFGSDFEKTGNSLD
M                K   *  X H   M              F   I
M                         R

WT IDFNSVHSGEKQIQIVNFKQIYYTVSVDAVKNPGDVFQDTVTVEDLKQRGISAERPLVY
M                                                R

WT ISSVAYGRQVYLKLETTSKSDEVEAAFEALIKGVKVAPQTEWKQILDNTEVKAVILGGD
M                      D    S M XX D

WT PSSGARVVTGKVDMVEDLIQEGSRFTADHPGLPISYTTSFLRDNVVATFQNSTDYVETK

WT VTAYRNGDLLLDHSGAYVAQYYITWDELSYDHQGKEVLTPKAWDRNGQDLTAHFTTSIP
M                            N                       E

WT LKGNVRNLSVKIRECTGLAWEWWRTVYEKTDLPLVRKRTISIWGTTLYPQVEDKVEND
M    *

WT= wtPLY sequence (wild-type)
M = known allelic or modified PLY sequence
X = amino acid deletion
* = amino acid insertion
```

FIGURE 1

*Exemplary "wtPLY" Amino Acid Sequences*

*Alleles and Modifications*

```
WT  MANKAVNDFILAMNYDKKKLLTHQGESIENRFIKEGNQLPDEFVVIERKKRSLSTNTSD
M               D

WT  ISVTATNDSRLYPGALLVVDETLLENNPTLLAVDRAPMTYSIDLPGLASSDSFLQVEDP

WT  SNSSVRGAVNDLLAKWHQDYGQVNNVPARMQYEKITAHSMEQLKVKFGSDFEKTGNSLD
M               K    *   X  H  M           F     I
M                                R

WT  IDFNSVHSGEKQIQIVNFKQIYYTVSVDAVKNPGDVFQDTVTVEDLKQRGISAERPLVY
M                                                        R

WT  ISSVAYGRQVYLKLETTSKSDEVEAAFEALIKGVKVAPQTEWKQILDNTEVKAVILGGD
M                D       S  M  XX D

WT  PSSGARVVTGKVDMVEDLIQEGSRFTADHPGLPISYTTSFLRDNVVATFQNSTDYVETK

WT  VTAYRNGDLLLDHSGAYVAQYYITWDELSYDHQGKEVLTPKAWDRNGQDLTAHFTTSIP
M                       N                    E

WT  LKGNVRNLSVKIRECTGLAWEWWRTVYEKTDLPLVRKRTISIWGTTLYPQVEDKVEND
M        *
```

WT= wtPLY sequence (wild-type)

M = known allelic or modified PLY sequence

X = amino acid deletion

* = amino acid insertion

Figure 2

In vitro *hemolytic activity of wtPLY and mPLY polypeptides modified at Gly293, assessed by toxin mediated lysis of sheep red blood cells*

*Mice immunized with PLY derivatives have decreased lung lobe injury mediated by PLY\**

\*Adj: indicates immunogenic composition contained alum adjuvant

*PlyD1 protein with a purity based on SDS-PAGE*

Lane 2: PlyD1 08-T-DP012
Lanes 3-10: PlyD1 4 ug loads

*Survival of CBA/J mice immunized three times with different doses of Adjuvanted Ply-D1**

*25µg, 10 µg, 1 µg, and 0.5µg dosages = not significant

SEQUENCE LISTING

<160> NUMBER OF SEQ ID NOS: 55

<210> SEQ ID NO 1
<211> LENGTH: 1416
<212> TYPE: DNA
<213> ORGANISM: Streptococcus pneumoniae

<400> SEQUENCE: 1

```
atggcaaata aagcagtaaa tgactttata ctagctatga attacgataa aaagaaactc      60
ttgacccatc agggagaaag tattgaaaat cgtttcatca agagggtaa tcagctaccc     120 gatgagtttg ttgttatcga agaaagaag cggagcttgt cgacaaatac aagtgatatt     180
tctgtaacag ctaccaacga cagtcgcctc tatcctggag cacttctcgt agtggatgag     240
accttgttag agaataatcc cactcttctt gcggttgatc gtgctccgat gacttatagt     300
attgatttgc ctggtttggc aagtagcgat agctttctcc aagtggaaga ccccagcaat     360
tcaagtgttc gcggagcggt aaacgatttg ttggctaagt ggcatcaaga ttatggtcag     420
gtcaataatg tcccagctag aatgcagtat gaaaaaataa cggctcacag catggaacaa     480
ctcaaggtca agtttggttc tgactttgaa agacagggga attctcttga tattgatttt     540
aactctgtcc attcaggtga aaagcagatt cagattgtta attttaagca gatttattat     600
acagtcagcg tagacgctgt taaaaatcca ggagatgtgt ttcaagatac tgtaacggta     660
gaggatttaa aacagagagg aatttctgca gagcgtcctt tggtctatat ttcgagtgtt     720
gcttatgggc gccaagtcta tctcaagttg gaaaccacga gtaagagtga tgaagtagag     780
gctgcttttg aagctttgat aaaaggagtc aaggtagctc ctcagacaga gtggaagcag     840
attttggaca atacagaagt gaaggcggtt attttagggg gcgacccaag ttcgggtgcc     900
cgagttgtaa caggcaaggt ggatatggta gaggacttga ttcaagaagg cagtcgcttt     960
acagcagatc atccaggctt gccgatttcc tatacaactt cttttttacg tgacaatgta    1020
gttgcgacct tcaaaacag tacagactat gttgagacta aggttacagc ttacagaaac    1080
ggagatttac tgctggatca tagtggtgcc tatgttgccc aatattatat tacttgggat    1140
gaattatcct atgatcatca aggtaaggaa gtcttgactc ctaaggcttg ggacagaaat    1200
gggcaggatt tgacggctca ctttaccact agtattcctt taaagggaa tgttcgtaat    1260 ctctctgtca aaattagaga gtgtaccggg cttgcctggg aatggtggcg tacggtttat    1320
gaaaaaaccg atttgccact agtgcgtaag cggacgattt ctatttgggg aacaactctc    1380
tatcctcagg tagaggataa ggtagaaaat gactag                              1416
```

<210> SEQ ID NO 2
<211> LENGTH: 471
<212> TYPE: PRT
<213> ORGANISM: Streptococcus pneumoniae

<400> SEQUENCE: 2

```
Met Ala Asn Lys Ala Val Asn Asp Phe Ile Leu Ala Met Asn Tyr Asp
 1               5                  10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
```

-continued

```
                35                  40                  45
Lys Lys Arg Ser Leu Ser Thr Asn Thr Ser Asp Ile Ser Val Thr Ala
 50                  55                  60

Thr Asn Asp Ser Arg Leu Tyr Pro Gly Ala Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
                115                 120                 125

Asp Leu Leu Ala Lys Trp His Gln Asp Tyr Gly Gln Val Asn Asn Val
                130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
                195                 200                 205

Asn Pro Gly Asp Val Phe Gln Asp Thr Val Thr Val Glu Asp Leu Lys
                210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
                290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
                355                 360                 365

Gly Ala Tyr Val Ala Gln Tyr Tyr Ile Thr Trp Asp Glu Leu Ser Tyr
                370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
                435                 440                 445

Arg Lys Arg Thr Ile Ser Ile Trp Gly Thr Thr Leu Tyr Pro Gln Val
450                 455                 460
```

Glu Asp Lys Val Glu Asn Asp
465                 470

<210> SEQ ID NO 3
<211> LENGTH: 471
<212> TYPE: PRT
<213> ORGANISM: Streptococcus pneumoniae

<400> SEQUENCE: 3

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser

```
                355                 360                 365
Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 4
<211> LENGTH: 470
<212> TYPE: PRT
<213> ORGANISM: Streptococcus pneumoniae

<400> SEQUENCE: 4

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Arg Met Gln Tyr Glu Lys Ile Thr Ala His Ser Met Glu Gln Leu
145                 150                 155                 160

Lys Val Lys Phe Gly Ser Asp Phe Glu Lys Thr Gly Asn Ser Leu Asp
                165                 170                 175

Ile Asp Phe Asn Ser Val His Ser Gly Glu Lys Gln Ile Gln Ile Val
            180                 185                 190

Asn Phe Lys Gln Ile Tyr Tyr Thr Val Ser Val Asp Ala Val Lys Asn
        195                 200                 205

Pro Gly Asp Val Phe Gln Asp Thr Val Thr Val Glu Asp Leu Lys Gln
    210                 215                 220

Arg Gly Ile Ser Ala Glu Arg Pro Leu Val Tyr Ile Ser Ser Val Ala
225                 230                 235                 240

Tyr Gly Arg Gln Val Tyr Leu Lys Leu Glu Thr Thr Ser Lys Ser Asp
                245                 250                 255
```

-continued

```
Glu Val Glu Ala Ala Phe Glu Ala Leu Ile Lys Gly Val Lys Val Ala
                260                 265                 270

Pro Gln Thr Glu Trp Lys Gln Ile Leu Asp Asn Thr Glu Val Lys Ala
            275                 280                 285

Val Ile Leu Gly Gly Asp Pro Ser Ser Gly Ala Arg Val Val Thr Gly
        290                 295                 300

Lys Val Asp Met Val Glu Asp Leu Ile Gln Glu Gly Ser Arg Phe Thr
305                 310                 315                 320

Ala Asp His Pro Gly Leu Pro Ile Ser Tyr Thr Thr Ser Phe Leu Arg
                325                 330                 335

Asp Asn Val Val Ala Thr Phe Gln Asn Ser Thr Asp Tyr Val Glu Thr
            340                 345                 350

Lys Val Thr Ala Tyr Arg Asn Gly Asp Leu Leu Asp His Ser Gly
        355                 360                 365

Ala Tyr Val Ala Gln Tyr Tyr Ile Thr Trp Asp Glu Leu Ser Tyr Asp
    370                 375                 380

His Gln Gly Lys Glu Val Leu Thr Pro Lys Ala Trp Asp Arg Asn Gly
385                 390                 395                 400

Gln Asp Leu Thr Ala His Phe Thr Thr Ser Ile Pro Leu Lys Gly Asn
                405                 410                 415

Val Arg Asn Leu Ser Val Lys Ile Arg Glu Cys Thr Gly Leu Ala Trp
            420                 425                 430

Glu Trp Trp Arg Thr Val Tyr Glu Lys Thr Asp Leu Pro Leu Val Arg
        435                 440                 445

Lys Arg Thr Ile Ser Ile Trp Gly Thr Thr Leu Tyr Pro Gln Val Glu
450                 455                 460

Asp Lys Val Glu Asn Asp
465                 470

<210> SEQ ID NO 5
<211> LENGTH: 471
<212> TYPE: PRT
<213> ORGANISM: Streptococcus pneumoniae

<400> SEQUENCE: 5

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Arg Arg Met Gln Tyr Glu Lys Ile Thr Ala His Ser Met Glu Gln
145                 150                 155                 160
```

```
Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 6
<211> LENGTH: 471
<212> TYPE: PRT
<213> ORGANISM: Streptococcus pneumoniae

<400> SEQUENCE: 6

Met Ala Asn Lys Ala Val Asn Asp Phe Ile Leu Ala Met Asn Tyr Asp
1               5                   10                  15

Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
```

```
                 50                  55                  60
Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                     85                  90                  95

Met Thr Tyr Ser Ile Asp Leu Pro Gly Leu Ala Ser Ser Asp Ser Phe
                    100                 105                 110

Leu Gln Val Glu Asp Pro Ser Asn Ser Ser Val Arg Gly Ala Val Asn
                115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                    165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                    245                 250                 255

Asp Glu Val Glu Ala Ala Phe Glu Ala Leu Met Lys Gly Val Lys Val
                260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                    325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
            370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                    405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
            450                 455                 460

Glu Asp Lys Val Glu Asn Asp
465                 470
```

<210> SEQ ID NO 7
<211> LENGTH: 471
<212> TYPE: PRT
<213> ORGANISM: Streptococcus pneumoniae

<400> SEQUENCE: 7

```
Met Ala Asn Lys Ala Val Asn Asp Phe Ile Leu Ala Met Asn Tyr Asp
1               5                   10                  15
Lys Lys Lys Leu Leu Thr His Gln Gly Glu Ser Ile Glu Asn Arg Phe
            20                  25                  30
Ile Lys Glu Gly Asn Gln Leu Pro Asp Glu Phe Val Val Ile Glu Arg
        35                  40                  45
Lys Lys Arg Ser Leu Ser Thr Asn Thr Ser Asp Ile Ser Val Thr Ala
    50                  55                  60
Thr Asn Asp Ser Arg Leu Tyr Pro Gly Ala Leu Val Val Asp Glu
65                  70                  75                  80
Thr Leu Leu Glu Asn Asn Pro Thr Leu Leu Ala Val Asp Arg Ala Pro
                85                  90                  95
Met Thr Tyr Ser Ile Asp Leu Pro Gly Leu Ala Ser Ser Asp Ser Phe
            100                 105                 110
Leu Gln Val Glu Asp Pro Ser Asn Ser Ser Val Arg Gly Ala Val Asn
        115                 120                 125
Asp Leu Leu Ala Lys Trp His Gln Asp Tyr Gly Gln Val Asn Asn Val
    130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
            180                 185                 190
Val Asn Phe Lys Gln Ile Tyr Tyr Thr Val Ser Val Asp Ala Val Lys
        195                 200                 205
Asn Pro Gly Asp Val Phe Gln Asp Thr Val Thr Val Glu Asp Leu Lys
    210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Asp Ala Ala Phe Glu Ala Leu Ile Lys Gly Val Lys Val
            260                 265                 270
Ala Pro Gln Thr Glu Trp Lys Gln Ile Leu Asp Asn Thr Glu Val Lys
        275                 280                 285
Ala Val Ile Leu Gly Gly Asp Pro Ser Ser Gly Ala Arg Val Val Thr
    290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
                325                 330                 335
Arg Asp Asn Val Val Ala Thr Phe Gln Asn Ser Thr Asp Tyr Val Glu
            340                 345                 350
Thr Lys Val Thr Ala Tyr Arg Asn Gly Asp Leu Leu Leu Asp His Ser
        355                 360                 365
Gly Ala Tyr Val Ala Gln Tyr Tyr Ile Thr Trp Asn Glu Leu Ser Tyr
```

```
                    370                 375                 380
Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 8
<211> LENGTH: 479
<212> TYPE: PRT
<213> ORGANISM: Streptococcus pneumoniae

<400> SEQUENCE: 8

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270
```

```
Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
        370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Leu Lys Gly Asn Val Arg Asn Leu Ser Val Lys
            420                 425                 430

Ile Arg Glu Cys Thr Gly Leu Ala Trp Glu Trp Trp Arg Thr Val Tyr
        435                 440                 445

Glu Lys Thr Asp Leu Pro Leu Val Arg Lys Arg Thr Ile Ser Ile Trp
    450                 455                 460

Gly Thr Thr Leu Tyr Pro Gln Val Glu Asp Lys Val Glu Asn Asp
465                 470                 475

<210> SEQ ID NO 9
<211> LENGTH: 469
<212> TYPE: PRT
<213> ORGANISM: Streptococcus pneumoniae

<400> SEQUENCE: 9

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln His Glu Lys Ile Thr Ala His Ser Met Glu Gln
145                 150                 155                 160

Leu Lys Val Lys Phe Gly Ser Asp Phe Glu Lys Ile Gly Asn Ser Leu
                165                 170                 175
```

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 10
<211> LENGTH: 469
<212> TYPE: PRT
<213> ORGANISM: Streptococcus pneumoniae

<400> SEQUENCE: 10

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu

```
                65                  70                  75                  80
        Thr Leu Leu Glu Asn Asn Pro Thr Leu Leu Ala Val Asp Arg Ala Pro
                            85                  90                  95

Met Thr Tyr Ser Ile Asp Leu Pro Gly Leu Ala Ser Ser Asp Ser Phe
                        100                 105                 110

Leu Gln Val Glu Asp Pro Ser Asn Ser Ser Val Arg Gly Ala Val Asn
                    115                 120                 125

Asp Leu Leu Ala Lys Trp His Gln Asp Tyr Gly Gln Val Asn Asn Val
                130                 135                 140

Pro Ala Arg Met Gln His Glu Lys Ile Thr Ala His Ser Met Glu Gln
        145                 150                 155                 160

Leu Lys Val Lys Phe Gly Ser Asp Phe Glu Lys Ile Gly Asn Ser Leu
                            165                 170                 175

Asp Ile Asp Phe Asn Ser Val His Ser Gly Glu Lys Gln Ile Gln Ile
                        180                 185                 190

Val Asn Phe Lys Gln Ile Tyr Tyr Thr Val Ser Val Asp Ala Val Lys
                    195                 200                 205

Asn Pro Gly Asp Val Phe Gln Asp Thr Val Thr Val Glu Asp Leu Arg
                210                 215                 220

Gln Arg Gly Ile Ser Ala Glu Arg Pro Leu Val Tyr Ile Ser Ser Val
        225                 230                 235                 240

Ala Tyr Gly Arg Gln Val Tyr Leu Lys Leu Glu Thr Thr Ser Lys Ser
                            245                 250                 255

Asp Glu Val Glu Ala Ala Phe Glu Ser Leu Ile Lys Gly Val Ala Pro
                        260                 265                 270

Gln Thr Glu Trp Lys Gln Ile Leu Asp Asn Thr Glu Val Lys Ala Val
                    275                 280                 285

Ile Leu Gly Gly Asp Pro Ser Ser Gly Ala Arg Val Val Thr Gly Lys
                290                 295                 300

Val Asp Met Val Glu Asp Leu Ile Gln Glu Gly Ser Arg Phe Thr Ala
        305                 310                 315                 320

Asp His Pro Gly Leu Pro Ile Ser Tyr Thr Thr Ser Phe Leu Arg Asp
                            325                 330                 335

Asn Val Val Ala Thr Phe Gln Asn Ser Thr Asp Tyr Val Glu Thr Lys
                        340                 345                 350

Val Thr Ala Tyr Arg Asn Gly Asp Leu Leu Leu Asp His Ser Gly Ala
                    355                 360                 365

Tyr Val Ala Gln Tyr Tyr Ile Thr Trp Asp Glu Leu Ser Tyr Asp His
                370                 375                 380

Gln Gly Lys Glu Val Leu Thr Pro Lys Ala Trp Asp Arg Asn Gly Gln
        385                 390                 395                 400

Asp Leu Thr Ala His Phe Thr Thr Ser Ile Pro Leu Lys Gly Asn Val
                            405                 410                 415

Arg Asn Leu Ser Val Lys Ile Arg Glu Cys Thr Gly Leu Ala Trp Glu
                        420                 425                 430

Trp Trp Arg Thr Val Tyr Glu Lys Thr Asp Leu Pro Leu Val Arg Lys
                    435                 440                 445

Arg Thr Ile Ser Ile Trp Gly Thr Thr Leu Tyr Pro Gln Val Glu Asp
                450                 455                 460

Lys Val Glu Asn Asp
        465

<210> SEQ ID NO 11
```

<211> LENGTH: 469
<212> TYPE: PRT
<213> ORGANISM: Streptococcus pneumoniae

<400> SEQUENCE: 11

| | | | | | | | | | | | | | | |
|---|---|---|---|---|---|---|---|---|---|---|---|---|---|---|
| Met | Ala | Asn | Lys | Ala | Val | Asn | Asp | Phe | Ile | Leu | Ala | Met | Asn | Tyr | Asp |
| 1 | | | | 5 | | | | | 10 | | | | | 15 | |
| Lys | Lys | Lys | Leu | Leu | Thr | His | Gln | Gly | Glu | Ser | Ile | Glu | Asn | Arg | Phe |
| | | | 20 | | | | | 25 | | | | | 30 | | |
| Ile | Lys | Glu | Gly | Asn | Gln | Leu | Pro | Asp | Glu | Phe | Val | Ile | Glu | Arg | |
| | | 35 | | | | | 40 | | | | | 45 | | | |
| Lys | Lys | Arg | Ser | Leu | Ser | Thr | Asn | Thr | Ser | Asp | Ile | Ser | Val | Thr | Ala |
| | 50 | | | | | 55 | | | | | 60 | | | | |
| Thr | Asn | Asp | Ser | Arg | Leu | Tyr | Pro | Gly | Ala | Leu | Leu | Val | Val | Asp | Glu |
| 65 | | | | | 70 | | | | | 75 | | | | | 80 |
| Thr | Leu | Leu | Glu | Asn | Asn | Pro | Thr | Leu | Leu | Ala | Val | Asp | Arg | Ala | Pro |
| | | | | 85 | | | | | 90 | | | | | 95 | |
| Met | Thr | Tyr | Ser | Ile | Asp | Leu | Pro | Gly | Leu | Ala | Ser | Ser | Asp | Ser | Phe |
| | | | 100 | | | | | 105 | | | | | 110 | | |
| Leu | Gln | Val | Glu | Asp | Pro | Ser | Asn | Ser | Ser | Val | Arg | Gly | Ala | Val | Asn |
| | | | 115 | | | | | 120 | | | | | 125 | | |
| Asp | Leu | Leu | Ala | Lys | Trp | His | Gln | Asp | Tyr | Gly | Gln | Val | Asn | Asn | Val |
| | 130 | | | | | 135 | | | | | 140 | | | | |
| Pro | Ala | Arg | Met | Gln | His | Glu | Lys | Ile | Thr | Ala | His | Ser | Met | Glu | Gln |
| 145 | | | | | 150 | | | | | 155 | | | | | 160 |
| Leu | Lys | Val | Lys | Phe | Gly | Ser | Asp | Phe | Glu | Lys | Ile | Gly | Asn | Ser | Leu |
| | | | | 165 | | | | | 170 | | | | | 175 | |
| Asp | Ile | Asp | Phe | Asn | Ser | Val | His | Ser | Gly | Glu | Lys | Gln | Ile | Gln | Ile |
| | | | 180 | | | | | 185 | | | | | 190 | | |
| Val | Asn | Phe | Lys | Gln | Ile | Tyr | Tyr | Thr | Val | Ser | Val | Asp | Ala | Val | Lys |
| | | | 195 | | | | | 200 | | | | | 205 | | |
| Asn | Pro | Gly | Asp | Val | Phe | Gln | Asp | Thr | Val | Thr | Val | Glu | Asp | Leu | Arg |
| | 210 | | | | | 215 | | | | | 220 | | | | |
| Gln | Arg | Gly | Ile | Ser | Ala | Glu | Arg | Pro | Leu | Val | Tyr | Ile | Ser | Ser | Val |
| 225 | | | | | 230 | | | | | 235 | | | | | 240 |
| Ala | Tyr | Gly | Arg | Gln | Val | Tyr | Leu | Lys | Leu | Glu | Thr | Thr | Ser | Lys | Ser |
| | | | | 245 | | | | | 250 | | | | | 255 | |
| Asp | Glu | Val | Glu | Ala | Ala | Phe | Glu | Ser | Leu | Ile | Lys | Gly | Val | Ala | Pro |
| | | | 260 | | | | | 265 | | | | | 270 | | |
| Gln | Thr | Glu | Trp | Lys | Gln | Ile | Leu | Asp | Asn | Thr | Glu | Val | Lys | Ala | Val |
| | | 275 | | | | | 280 | | | | | 285 | | | |
| Ile | Leu | Gly | Gly | Asp | Pro | Ser | Ser | Gly | Ala | Arg | Val | Val | Thr | Gly | Lys |
| | 290 | | | | | 295 | | | | | 300 | | | | |
| Val | Asp | Met | Val | Glu | Asp | Leu | Ile | Gln | Glu | Gly | Ser | Arg | Phe | Thr | Ala |
| 305 | | | | | 310 | | | | | 315 | | | | | 320 |
| Asp | His | Pro | Gly | Leu | Pro | Ile | Ser | Tyr | Thr | Thr | Ser | Phe | Leu | Arg | Asp |
| | | | | 325 | | | | | 330 | | | | | 335 | |
| Asn | Val | Val | Ala | Thr | Phe | Gln | Asn | Ser | Thr | Asp | Tyr | Val | Glu | Thr | Lys |
| | | | 340 | | | | | 345 | | | | | 350 | | |
| Val | Thr | Ala | Tyr | Arg | Asn | Gly | Asp | Leu | Leu | Asp | His | Ser | Gly | Ala | |
| | | 355 | | | | | 360 | | | | | 365 | | | |
| Tyr | Val | Ala | Gln | Tyr | Tyr | Ile | Thr | Trp | Asp | Glu | Leu | Ser | Tyr | Asp | His |
| | 370 | | | | | 375 | | | | | 380 | | | | |
| Gln | Gly | Lys | Glu | Val | Leu | Thr | Pro | Lys | Ala | Trp | Asp | Arg | Asn | Gly | Gln |

```
              385                 390                 395                 400
Asp Leu Thr Ala His Phe Thr Thr Ser Ile Pro Leu Lys Gly Asn Val
                    405                 410                 415

Arg Asn Leu Ser Val Lys Ile Arg Glu Cys Thr Gly Leu Ala Trp Glu
                420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
450                 455                 460

Lys Val Glu Asn Asp
465

<210> SEQ ID NO 12
<211> LENGTH: 471
<212> TYPE: PRT
<213> ORGANISM: Streptococcus pneumoniae

<400> SEQUENCE: 12

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
        50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285
```

```
Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Glu Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 13
<211> LENGTH: 471
<212> TYPE: PRT
<213> ORGANISM: Streptococcus pneumoniae

<400> SEQUENCE: 13

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190
```

```
Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Phe Leu
            325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
        370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470

<210> SEQ ID NO 14
<211> LENGTH: 471
<212> TYPE: PRT
<213> ORGANISM: Streptococcus pneumoniae

<400> SEQUENCE: 14

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
```

```
                     85                  90                  95
Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Lys
        210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Asp Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
        370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470

<210> SEQ ID NO 15
<211> LENGTH: 469
<212> TYPE: PRT
<213> ORGANISM: Streptococcus pneumoniae
```

<400> SEQUENCE: 15

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln His Glu Lys Ile Thr Ala His Ser Met Glu Gln
145                 150                 155                 160

Leu Lys Val Lys Phe Gly Ser Asp Phe Glu Lys Ile Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
```

```
            405                 410                 415
Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
            450                 455                 460

Lys Val Glu Asn Asp
465

<210> SEQ ID NO 16
<211> LENGTH: 471
<212> TYPE: PRT
<213> ORGANISM: Streptococcus pneumoniae

<400> SEQUENCE: 16

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Lys Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300
```

```
Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 17
<211> LENGTH: 469
<212> TYPE: PRT
<213> ORGANISM: Streptococcus pneumoniae

<400> SEQUENCE: 17

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Met Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205
```

Asn Pro Gly Asp Val Phe Gln Asp Thr Val Thr Val Glu Asp Leu Lys
            210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Asp His Ser Gly Ala
        355                 360                 365

Tyr Val Ala Gln Tyr Tyr Ile Thr Trp Asn Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 18
<211> LENGTH: 469
<212> TYPE: PRT
<213> ORGANISM: Streptococcus pneumoniae

<400> SEQUENCE: 18

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe

```
            100                 105                 110
Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Met Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Asp His Ser Gly Ala
        355                 360                 365

Tyr Val Ala Gln Tyr Tyr Ile Thr Trp Asn Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465
```

<210> SEQ ID NO 19
<211> LENGTH: 471
<212> TYPE: PRT
<213> ORGANISM: Streptococcus pneumoniae

<400> SEQUENCE: 19

```
Met Ala Asn Lys Ala Val Asn Asp Phe Ile Leu Ala Met Asp Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
50              55                  60

Thr Asn Asp Ser Arg Leu Tyr Pro Gly Ala Leu Leu Val Val Asp Glu
65                  70                  75                  80

Thr Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
            130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
            195                 200                 205

Asn Pro Gly Asp Val Phe Gln Asp Thr Val Thr Val Glu Asp Leu Arg
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
            290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asp Glu Leu Ser Tyr
            370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
```

```
              420                 425                 430
Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470

<210> SEQ ID NO 20
<211> LENGTH: 469
<212> TYPE: PRT
<213> ORGANISM: Streptococcus pneumoniae

<400> SEQUENCE: 20

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Ile Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320
```

```
Asp His Pro Gly Leu Pro Ile Ser Tyr Thr Thr Ser Phe Leu Arg Asp
            325                 330                 335

Asn Val Val Ala Thr Phe Gln Asn Ser Thr Asp Tyr Val Glu Thr Lys
        340                 345                 350

Val Thr Ala Tyr Arg Asn Gly Asp Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 21
<211> LENGTH: 469
<212> TYPE: PRT
<213> ORGANISM: Streptococcus pneumoniae

<400> SEQUENCE: 21

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln His Glu Lys Ile Thr Ala His Ser Met Glu Gln
145                 150                 155                 160

Leu Lys Val Lys Phe Gly Ser Asp Phe Glu Lys Ile Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220
```

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
            275                 280                 285

Ile Leu Gly Gly Asp Pro Ser Ser Gly Ala Arg Val Val Thr Gly Lys
            290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
                340                 345                 350

Val Thr Ala Tyr Arg Asn Gly Asp Leu Leu Leu Asp His Ser Gly Ala
                355                 360                 365

Tyr Val Ala Gln Tyr Tyr Ile Thr Trp Asp Glu Leu Ser Tyr Asp His
370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
                420                 425                 430

Trp Trp Arg Thr Val Tyr Glu Lys Thr Asp Leu Pro Leu Val Arg Lys
                435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 22
<211> LENGTH: 469
<212> TYPE: PRT
<213> ORGANISM: Streptococcus pneumoniae

<400> SEQUENCE: 22

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn

```
                    115                 120                 125
Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Phe Asp Phe Glu Lys Ile Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 23
<211> LENGTH: 471
<212> TYPE: PRT
<213> ORGANISM: Streptococcus pneumoniae

<400> SEQUENCE: 23

Met Ala Asn Lys Ala Val Asn Asp Phe Ile Leu Ala Met Asn Tyr Asp
1               5                   10                  15
```

```
Lys Lys Lys Leu Leu Thr His Gln Gly Glu Ser Ile Glu Asn Arg Phe
             20                  25                  30

Ile Lys Glu Gly Asn Gln Leu Pro Asp Glu Phe Val Val Ile Glu Arg
         35                  40                  45

Lys Lys Arg Ser Leu Ser Thr Asn Thr Ser Asp Ile Ser Val Thr Ala
     50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
             100                 105                 110

Leu Gln Val Glu Asp Pro Ser Asn Ser Ser Val Arg Gly Ala Val Asn
         115                 120                 125

Asp Leu Leu Ala Lys Trp His Gln Asp Tyr Gly Gln Val Asn Asn Val
     130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                 165                 170                 175

Asp Ile Asp Phe Asn Ser Val His Ser Gly Glu Lys Gln Ile Gln Ile
             180                 185                 190

Val Asn Phe Lys Gln Ile Tyr Tyr Thr Val Ser Val Asp Ala Val Lys
         195                 200                 205

Asn Pro Gly Asp Val Phe Gln Asp Thr Val Thr Val Glu Asp Leu Lys
     210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                 245                 250                 255

Asp Glu Val Glu Ala Ala Phe Glu Ala Leu Ile Lys Gly Val Lys Val
             260                 265                 270

Ala Pro Gln Thr Glu Trp Lys Gln Ile Leu Asp Asn Thr Glu Val Lys
         275                 280                 285

Ala Val Ile Leu Gly Gly Asp Pro Ser Ser Gly Ala Arg Val Val Thr
     290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                 325                 330                 335

Arg Asp Asn Val Val Ala Thr Phe Gln Asn Ser Thr Asp Tyr Val Glu
             340                 345                 350

Thr Lys Val Thr Ala Tyr Arg Asn Gly Asp Leu Leu Leu Asp His Ser
         355                 360                 365

Gly Ala Tyr Val Ala Gln Tyr Tyr Ile Thr Trp Asn Glu Leu Ser Tyr
     370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                 405                 410                 415

Asn Val Arg Asn Leu Ser Val Lys Ile Arg Glu Cys Thr Gly Leu Ala
             420                 425                 430

Trp Glu Trp Trp Arg Thr Val Tyr Glu Lys Thr Asp Leu Pro Leu Val
```

```
                 435                 440                 445
Arg Lys Arg Thr Ile Ser Ile Trp Gly Thr Thr Leu Tyr Pro Gln Val
    450                 455                 460

Glu Asp Lys Val Glu Asn Asp
465                 470
```

<210> SEQ ID NO 24
<211> LENGTH: 471
<212> TYPE: PRT
<213> ORGANISM: Streptococcus pneumoniae

<400> SEQUENCE: 24

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335
```

```
Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
        370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 25
<211> LENGTH: 471
<212> TYPE: PRT
<213> ORGANISM: Streptococcus pneumoniae

<400> SEQUENCE: 25

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His His Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240
```

```
Ala Tyr Gly Arg Gln Val Tyr Leu Lys Leu Glu Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 26
<211> LENGTH: 471
<212> TYPE: PRT
<213> ORGANISM: Streptococcus pneumoniae

<400> SEQUENCE: 26

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Gly Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
```

```
                130                 135                 140
Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
                180                 185                 190

Val Asn Phe Lys Gln Ile Tyr Tyr Thr Val Ser Val Asp Ala Val Lys
                195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
                260                 265                 270

Ala Pro Gln Thr Glu Trp Lys Gln Ile Leu Asp Asn Thr Glu Val Lys
                275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
                340                 345                 350

Thr Lys Val Thr Ala Tyr Arg Asn Gly Asp Leu Leu Asp His Ser
                355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
                420                 425                 430

Trp Glu Trp Trp Arg Thr Val Tyr Glu Lys Thr Asp Leu Pro Leu Val
                435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 27
<211> LENGTH: 471
<212> TYPE: PRT
<213> ORGANISM: Streptococcus pneumoniae

<400> SEQUENCE: 27

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30
```

```
Ile Lys Glu Gly Asn Gln Leu Pro Asp Glu Phe Val Ile Glu Arg
        35                  40                  45

Lys Lys Arg Ser Leu Ser Thr Asn Thr Ser Asp Ile Ser Val Thr Ala
 50                  55                  60

Thr Asn Asp Ser Arg Leu Tyr Pro Gly Ala Leu Leu Val Val Asp Glu
 65                  70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
        210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
        370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
```

```
                    450                 455                 460
Glu Asp Lys Val Glu Asn Asp
465                 470

<210> SEQ ID NO 28
<211> LENGTH: 471
<212> TYPE: PRT
<213> ORGANISM: Streptococcus pneumoniae

<400> SEQUENCE: 28

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

Lys Lys Arg Ser Leu Ser Thr Asn Thr Ser Asp Ile Ser Val Thr Ala
        50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350
```

```
Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470

<210> SEQ ID NO 29
<211> LENGTH: 471
<212> TYPE: PRT
<213> ORGANISM: Streptococcus pneumoniae

<400> SEQUENCE: 29

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255
```

```
Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 30
<211> LENGTH: 471
<212> TYPE: PRT
<213> ORGANISM: Streptococcus pneumoniae

<400> SEQUENCE: 30

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
```

145                 150                 155                 160
Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 31
<211> LENGTH: 471
<212> TYPE: PRT
<213> ORGANISM: Streptococcus pneumoniae

<400> SEQUENCE: 31

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
                20                  25                  30

Ile Lys Glu Gly Asn Gln Leu Pro Asp Glu Phe Val Val Ile Glu Arg
            35                  40                  45

```
Lys Lys Arg Ser Leu Ser Thr Asn Thr Ser Asp Ile Ser Val Thr Ala
     50                  55                  60
Thr Asn Asp Ser Arg Leu Tyr Pro Gly Ala Leu Leu Val Val Asp Glu
 65              70                  75                  80
Thr Leu Leu Glu Asn Asn Pro Thr Leu Leu Ala Val Asp Arg Ala Pro
                 85                  90                  95
Met Thr Tyr Ser Ile Asp Leu Pro Gly Leu Ala Ser Ser Asp Ser Phe
                100                 105                 110
Leu Gln Val Glu Asp Pro Ser Asn Ser Ser Val Arg Gly Ala Val Asn
            115                 120                 125
Asp Leu Leu Ala Lys Trp His Gln Asp Tyr Gly Gln Val Asn Asn Val
        130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
                180                 185                 190
Val Asn Phe Lys Gln Ile Tyr Tyr Thr Val Ser Val Asp Ala Val Lys
            195                 200                 205
Asn Pro Gly Asp Val Phe Gln Asp Thr Val Thr Val Glu Asp Leu Lys
        210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Phe Glu Ala Leu Ile Lys Gly Val Lys Val
            260                 265                 270
Ala Pro Gln Thr Glu Trp Lys Gln Ile Leu Asp Asn Thr Glu Val Lys
        275                 280                 285
Ala Val Ile Leu Gly Gly Asp Pro Ser Ser Gly Ala Arg Val Val Thr
290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
                325                 330                 335
Arg Asp Asn Val Val Ala Thr Phe Gln Asn Ser Thr Asp Tyr Val Glu
            340                 345                 350
Thr Lys Val Thr Ala Tyr Arg Asn Gly Asp Leu Leu Leu Asp His Ser
        355                 360                 365
Gly Ala Tyr Val Ala Gln Tyr Tyr Ile Thr Trp Asn Glu Leu Ser Tyr
370                 375                 380
Asp His Gln Gly Lys Glu Val Leu Thr Pro Lys Ala Trp Asp Arg Asn
385                 390                 395                 400
Gly Gln Asp Leu Thr Ala His Phe Thr Thr Ser Ile Pro Leu Lys Gly
                405                 410                 415
Asn Val Arg Asn Leu Ser Val Lys Ile Arg Glu Cys Thr Gly Leu Ala
            420                 425                 430
Trp Glu Trp Trp Arg Thr Val Tyr Glu Lys Thr Asp Leu Pro Leu Val
        435                 440                 445
Arg Lys Arg Thr Ile Ser Ile Trp Gly Thr Thr Leu Tyr Pro Gln Val
450                 455                 460
Glu Asp Lys Val Glu Asn Asp
```

465       470

<210> SEQ ID NO 32
<211> LENGTH: 471
<212> TYPE: PRT
<213> ORGANISM: Streptococcus pneumoniae

<400> SEQUENCE: 32

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

```
Gly Ala Tyr Val Ala Gln Tyr Tyr Ile Thr Trp Asp Glu Leu Ser Tyr
            370                 375                 380
Asp His Gln Gly Lys Glu Val Leu Thr Pro Lys Ala Trp Asp Arg Asn
385                 390                 395                 400
Gly Gln Asp Leu Thr Ala His Phe Thr Thr Ser Ile Pro Leu Lys Gly
                405                 410                 415
Asn Val Arg Asn Leu Ser Val Lys Ile Arg Glu Cys Thr Gly Leu Ala
            420                 425                 430
Trp Glu Trp Trp Arg Thr Val Tyr Glu Lys Thr Asp Leu Pro Leu Val
                435                 440                 445
Arg Lys Arg Thr Ile Ser Ile Trp Gly Thr Thr Leu Tyr Pro Gln Val
450                 455                 460
Glu Asp Lys Val Glu Asn Asp
465                 470

<210> SEQ ID NO 33
<211> LENGTH: 471
<212> TYPE: PRT
<213> ORGANISM: Streptococcus pneumoniae

<400> SEQUENCE: 33

Met Ala Asn Lys Ala Val Asn Asp Phe Ile Leu Ala Met Asn Tyr Asp
1               5                   10                  15
Lys Lys Lys Leu Leu Thr His Gln Gly Glu Ser Ile Glu Asn Arg Phe
            20                  25                  30
Ile Lys Glu Gly Asn Gln Leu Pro Asp Glu Phe Val Val Ile Glu Arg
        35                  40                  45
Lys Lys Arg Ser Leu Ser Thr Asn Thr Ser Asp Ile Ser Val Thr Ala
    50                  55                  60
Thr Asn Asp Ser Arg Leu Tyr Pro Gly Ala Leu Leu Val Val Asp Glu
65                  70                  75                  80
Thr Leu Leu Glu Asn Asn Pro Thr Leu Leu Ala Val Asp Arg Ala Pro
                85                  90                  95
Met Thr Tyr Ser Ile Asp Leu Pro Gly Leu Ala Ser Ser Asp Ser Phe
            100                 105                 110
Leu Gln Val Glu Asp Pro Ser Asn Ser Ser Val Arg Gly Ala Val Asn
        115                 120                 125
Asp Leu Leu Ala Lys Trp His Gln Asp Tyr Gly Gln Val Asn Asn Val
    130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
            180                 185                 190
Val Asn Phe Lys Gln Ile Tyr Tyr Thr Val Ser Val Asp Ala Val Lys
        195                 200                 205
Asn Pro Gly Asp Val Phe Gln Asp Thr Val Thr Val Glu Asp Leu Lys
    210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Phe Glu Ala Leu Ile Lys Gly Val Lys Val
            260                 265                 270
```

-continued

```
Ala Pro Gln Thr Glu Trp Lys Gln Ile Leu Asp Asn Thr Glu Val Lys
            275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
            325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
            355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
            450                 455                 460

Glu Asp Lys Val Glu Asn Asp
465                 470

<210> SEQ ID NO 34
<211> LENGTH: 471
<212> TYPE: PRT
<213> ORGANISM: Streptococcus pneumoniae

<400> SEQUENCE: 34

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
```

165                 170                 175
Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
            245                 250                 255

Asp Glu Val Glu Ala Ala Phe Glu Ala Leu Ile Lys Gly Val Lys Val
        260                 265                 270

Ala Pro Gln Thr Glu Trp Lys Gln Ile Leu Asp Asn Thr Glu Val Lys
    275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
            325                 330                 335

Arg Asp Asn Val Val Ala Thr Phe Gln Asn Ser Thr Asp Tyr Val Glu
        340                 345                 350

Thr Lys Val Thr Ala Tyr Arg Asn Gly Asp Leu Leu Leu Asp His Ser
    355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
        420                 425                 430

Trp Glu Trp Trp Arg Thr Val Tyr Glu Lys Thr Asp Leu Pro Leu Val
    435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 35
<211> LENGTH: 471
<212> TYPE: PRT
<213> ORGANISM: Streptococcus pneumoniae

<400> SEQUENCE: 35

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

-continued

```
Thr Asn Asp Ser Arg Leu Tyr Pro Gly Ala Leu Val Val Asp Glu
 65              70                  75                  80

Thr Leu Leu Glu Asn Asn Pro Thr Leu Leu Ala Val Asp Arg Ala Pro
                 85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
        290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470
```

<210> SEQ ID NO 36
<211> LENGTH: 471
<212> TYPE: PRT
<213> ORGANISM: Streptococcus pneumoniae

<400> SEQUENCE: 36

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
370                 375                 380

```
Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
        420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
        450                 455                 460

Glu Asp Lys Val Glu Asn Asp
465                 470

<210> SEQ ID NO 37
<211> LENGTH: 471
<212> TYPE: PRT
<213> ORGANISM: Streptococcus pneumoniae

<400> SEQUENCE: 37

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Ser Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285
```

```
Ala Val Ile Leu Gly Gly Asp Pro Ser Ser Gly Ala Arg Val Val Thr
            290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
            325                 330                 335
Arg Asp Asn Val Val Ala Thr Phe Gln Asn Ser Thr Asp Tyr Val Glu
            340                 345                 350
Thr Lys Val Thr Ala Tyr Arg Asn Gly Asp Leu Leu Leu Asp His Ser
            355                 360                 365
Gly Ala Tyr Val Ala Gln Tyr Tyr Ile Thr Trp Asp Glu Leu Ser Tyr
            370                 375                 380
Asp His Gln Gly Lys Glu Val Leu Thr Pro Lys Ala Trp Asp Arg Asn
385                 390                 395                 400
Gly Gln Asp Leu Thr Ala His Phe Thr Thr Ser Ile Pro Leu Lys Gly
            405                 410                 415
Asn Val Arg Asn Leu Ser Val Lys Ile Arg Glu Cys Thr Gly Leu Ala
            420                 425                 430
Trp Glu Trp Trp Arg Thr Val Tyr Glu Lys Thr Asp Leu Pro Leu Val
            435                 440                 445
Arg Lys Arg Thr Ile Ser Ile Trp Gly Thr Thr Leu Tyr Pro Gln Val
            450                 455                 460
Glu Asp Lys Val Glu Asn Asp
465                 470

<210> SEQ ID NO 38
<211> LENGTH: 469
<212> TYPE: PRT
<213> ORGANISM: Streptococcus pneumoniae

<400> SEQUENCE: 38

Met Ala Asn Lys Ala Val Asn Asp Phe Ile Leu Ala Met Asn Tyr Asp
1               5                   10                  15
Lys Lys Lys Leu Leu Thr His Gln Gly Glu Ser Ile Glu Asn Arg Phe
            20                  25                  30
Ile Lys Glu Gly Asn Gln Leu Pro Asp Glu Phe Val Ile Glu Arg
            35                  40                  45
Lys Lys Arg Ser Leu Ser Thr Asn Thr Ser Asp Ile Ser Val Thr Ala
            50                  55                  60
Thr Asn Asp Ser Arg Leu Tyr Pro Gly Ala Leu Leu Val Asp Glu
65                  70                  75                  80
Thr Leu Leu Glu Asn Asn Pro Thr Leu Leu Ala Val Asp Arg Ala Pro
            85                  90                  95
Met Thr Tyr Ser Ile Asp Leu Pro Gly Leu Ala Ser Ser Asp Ser Phe
            100                 105                 110
Leu Gln Val Glu Asp Pro Ser Asn Ser Ser Val Arg Gly Ala Val Asn
            115                 120                 125
Asp Leu Leu Ala Lys Trp His Gln Asp Tyr Gly Gln Val Asn Asn Val
            130                 135                 140
Pro Ala Arg Met Gln Tyr Glu Lys Ile Met Ala His Ser Met Glu Gln
145                 150                 155                 160
Leu Lys Val Lys Phe Gly Ser Asp Phe Glu Lys Thr Gly Asn Ser Leu
            165                 170                 175
Asp Ile Asp Phe Asn Ser Val His Ser Gly Glu Lys Gln Ile Gln Ile
```

```
                180              185              190
Val Asn Phe Lys Gln Ile Tyr Tyr Thr Val Ser Val Asp Ala Val Lys
            195              200              205
Asn Pro Gly Asp Val Phe Gln Asp Thr Val Thr Val Glu Asp Leu Lys
        210              215              220
Gln Arg Gly Ile Ser Ala Glu Arg Pro Leu Val Tyr Ile Ser Ser Val
225              230              235              240
Ala Tyr Gly Arg Gln Val Tyr Leu Lys Leu Glu Thr Thr Ser Lys Ser
            245              250              255
Asp Glu Val Glu Ala Ala Phe Glu Ser Leu Ile Lys Gly Val Ala Pro
        260              265              270
Gln Thr Glu Trp Lys Gln Ile Leu Asp Asn Thr Glu Val Lys Ala Val
            275              280              285
Ile Leu Gly Gly Asp Pro Ser Ser Gly Ala Arg Val Val Thr Gly Lys
        290              295              300
Val Asp Met Val Glu Asp Leu Ile Gln Glu Gly Ser Arg Phe Thr Ala
305              310              315              320
Asp His Pro Gly Leu Pro Ile Ser Tyr Thr Thr Ser Phe Leu Arg Asp
            325              330              335
Asn Val Val Ala Thr Phe Gln Asn Ser Thr Asp Tyr Val Glu Thr Lys
        340              345              350
Val Thr Ala Tyr Arg Asn Gly Asp Leu Leu Asp His Ser Gly Ala
            355              360              365
Tyr Val Ala Gln Tyr Tyr Ile Thr Trp Asp Glu Leu Ser Tyr Asp His
        370              375              380
Gln Gly Lys Glu Val Leu Thr Pro Lys Ala Trp Asp Arg Asn Gly Gln
385              390              395              400
Asp Leu Thr Ala His Phe Thr Thr Ser Ile Pro Leu Lys Gly Asn Val
            405              410              415
Arg Asn Leu Ser Val Lys Ile Arg Glu Cys Thr Gly Leu Ala Trp Glu
        420              425              430
Trp Trp Arg Thr Val Tyr Glu Lys Thr Asp Leu Pro Leu Val Arg Lys
            435              440              445
Arg Thr Ile Ser Ile Trp Gly Thr Thr Leu Tyr Pro Gln Val Glu Asp
        450              455              460
Lys Val Glu Asn Asp
465

<210> SEQ ID NO 39
<211> LENGTH: 469
<212> TYPE: PRT
<213> ORGANISM: Streptococcus pneumoniae

<400> SEQUENCE: 39

Met Ala Asn Lys Ala Val Asn Asp Phe Ile Leu Ala Met Asn Tyr Asp
1               5                   10                  15
Lys Lys Lys Leu Leu Thr His Gln Gly Glu Ser Ile Glu Asn Arg Phe
            20                  25                  30
Ile Lys Glu Gly Asn Gln Leu Pro Asp Glu Phe Val Val Ile Glu Arg
        35                  40                  45
Lys Lys Arg Ser Leu Ser Thr Asn Thr Ser Asp Ile Ser Val Thr Ala
    50                  55                  60
Thr Asn Asp Ser Arg Leu Tyr Pro Gly Ala Leu Leu Val Asp Glu
65                  70                  75                  80
```

```
Thr Leu Leu Glu Asn Asn Pro Thr Leu Leu Ala Val Asp Arg Ala Pro
             85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Ile Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Arg
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 40
<211> LENGTH: 469
<212> TYPE: PRT
```

<213> ORGANISM: Streptococcus pneumoniae

<400> SEQUENCE: 40

| | | | | | | | | | | | | | | |
|---|---|---|---|---|---|---|---|---|---|---|---|---|---|---|
|Met|Ala|Asn|Lys|Ala|Val|Asn|Asp|Phe|Ile|Leu|Ala|Met|Asn|Tyr|Asp|
|1| | | |5| | | | |10| | | | |15| |
|Lys|Lys|Lys|Leu|Leu|Thr|His|Gln|Gly|Glu|Ser|Ile|Glu|Asn|Arg|Phe|
| | | |20| | | | |25| | | | |30| | |
|Ile|Lys|Glu|Gly|Asn|Gln|Leu|Pro|Asp|Glu|Phe|Val|Val|Ile|Glu|Arg|
| | |35| | | | |40| | | | |45| | | |
|Lys|Lys|Arg|Ser|Leu|Ser|Thr|Asn|Thr|Ser|Asp|Ile|Ser|Val|Thr|Ala|
| |50| | | | |55| | | | |60| | | | |
|Thr|Asn|Asp|Ser|Arg|Leu|Tyr|Pro|Gly|Ala|Leu|Leu|Val|Val|Asp|Glu|
|65| | | | |70| | | | |75| | | | |80|
|Thr|Leu|Leu|Glu|Asn|Asn|Pro|Thr|Leu|Leu|Ala|Val|Asp|Arg|Ala|Pro|
| | | | |85| | | | |90| | | | |95| |
|Met|Thr|Tyr|Ser|Ile|Asp|Leu|Pro|Gly|Leu|Ala|Ser|Ser|Asp|Ser|Phe|
| | | |100| | | | |105| | | | |110| | |
|Leu|Gln|Val|Glu|Asp|Pro|Ser|Asn|Ser|Ser|Val|Arg|Gly|Ala|Val|Asn|
| | | |115| | | | |120| | | | |125| | |
|Asp|Leu|Leu|Ala|Lys|Trp|His|Gln|Asp|Tyr|Gly|Gln|Val|Asn|Asn|Val|
| |130| | | | |135| | | | |140| | | | |
|Pro|Ala|Arg|Met|Gln|His|Glu|Lys|Ile|Thr|Ala|His|Ser|Met|Glu|Gln|
|145| | | | |150| | | | |155| | | | |160|
|Leu|Lys|Val|Lys|Phe|Gly|Ser|Asp|Phe|Glu|Lys|Ile|Gly|Asn|Ser|Leu|
| | | | |165| | | | |170| | | | |175| |
|Asp|Ile|Asp|Phe|Asn|Ser|Val|His|Ser|Gly|Glu|Lys|Gln|Ile|Gln|Ile|
| | | |180| | | | |185| | | | |190| | |
|Val|Asn|Phe|Lys|Gln|Ile|Tyr|Tyr|Thr|Val|Ser|Val|Asp|Ala|Val|Lys|
| | |195| | | | |200| | | | |205| | | |
|Asn|Pro|Gly|Asp|Val|Phe|Gln|Asp|Thr|Val|Thr|Val|Glu|Asp|Leu|Arg|
| |210| | | | |215| | | | |220| | | | |
|Gln|Arg|Gly|Ile|Ser|Ala|Glu|Arg|Pro|Leu|Val|Tyr|Ile|Ser|Ser|Val|
|225| | | | |230| | | | |235| | | | |240|
|Ala|Tyr|Gly|Arg|Gln|Val|Tyr|Leu|Lys|Leu|Glu|Thr|Thr|Ser|Lys|Ser|
| | | | |245| | | | |250| | | | |255| |
|Asp|Glu|Val|Glu|Ala|Ala|Phe|Glu|Ser|Leu|Ile|Lys|Gly|Val|Ala|Pro|
| | | |260| | | | |265| | | | |270| | |
|Gln|Thr|Glu|Trp|Lys|Gln|Ile|Leu|Asp|Asn|Thr|Glu|Val|Lys|Ala|Val|
| | |275| | | | |280| | | | |285| | | |
|Ile|Leu|Gly|Gly|Asp|Pro|Ser|Ser|Gly|Ala|Arg|Val|Val|Thr|Gly|Lys|
| |290| | | | |295| | | | |300| | | | |
|Val|Asp|Met|Val|Glu|Asp|Leu|Ile|Gln|Glu|Gly|Ser|Arg|Phe|Thr|Ala|
|305| | | | |310| | | | |315| | | | |320|
|Asp|His|Pro|Gly|Leu|Pro|Ile|Ser|Tyr|Thr|Thr|Ser|Phe|Leu|Arg|Asp|
| | | | |325| | | | |330| | | | |335| |
|Asn|Val|Val|Ala|Thr|Phe|Gln|Asn|Ser|Thr|Asp|Tyr|Val|Glu|Thr|Lys|
| | | |340| | | | |345| | | | |350| | |
|Val|Thr|Ala|Tyr|Arg|Asn|Gly|Asp|Leu|Leu|Leu|Asp|His|Ser|Gly|Ala|
| | |355| | | | |360| | | | |365| | | |
|Tyr|Val|Ala|Gln|Tyr|Tyr|Ile|Thr|Trp|Asp|Glu|Leu|Ser|Tyr|Asp|His|
| |370| | | | |375| | | | |380| | | | |
|Gln|Gly|Lys|Glu|Val|Leu|Thr|Pro|Lys|Ala|Trp|Asp|Arg|Asn|Gly|Gln|
|385| | | | |390| | | | |395| | | | |400|

```
Asp Leu Thr Ala His Phe Thr Thr Ser Ile Pro Leu Lys Gly Asn Val
            405                 410                 415

Arg Asn Leu Ser Val Lys Ile Arg Glu Cys Thr Gly Leu Ala Trp Glu
        420                 425                 430

Trp Trp Arg Thr Val Tyr Glu Lys Thr Asp Leu Pro Leu Val Arg Lys
            435                 440                 445

Arg Thr Ile Ser Ile Trp Gly Thr Thr Leu Tyr Pro Gln Val Glu Asp
        450                 455                 460

Lys Val Glu Asn Asp
465

<210> SEQ ID NO 41
<211> LENGTH: 471
<212> TYPE: PRT
<213> ORGANISM: Streptococcus pneumoniae

<400> SEQUENCE: 41

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Ile Glu Arg
        35                  40                  45

Lys Lys Arg Ser Leu Ser Thr Asn Thr Ser Asp Ile Ser Val Thr Ala
50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
            85                  90                  95

Met Thr Tyr Ser Ile Asp Leu Pro Gly Leu Ala Ser Ser Asp Ser Phe
        100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
        290                 295                 300
```

-continued

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
            325                 330                 335

Arg Asp Asn Val Val Ala Thr Phe Gln Asn Ser Thr Tyr Val Glu
        340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asn Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
            405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
            435                 440                 445

Arg Lys Arg Thr Ile Ser Ile Trp Gly Thr Thr Leu Tyr Pro Gln Val
450                 455                 460

Glu Asp Lys Val Glu Asn Asp
465                 470

<210> SEQ ID NO 42
<211> LENGTH: 469
<212> TYPE: PRT
<213> ORGANISM: Streptococcus pneumoniae

<400> SEQUENCE: 42

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln His Glu Lys Ile Thr Ala His Ser Met Glu Gln
145                 150                 155                 160

Leu Lys Val Lys Phe Gly Ser Asp Phe Glu Lys Ile Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys

```
                195                 200                 205
Asn Pro Gly Asp Val Phe Gln Asp Thr Val Thr Val Glu Asp Leu Arg
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ser Leu Ile Lys Gly Val Ala Pro
            260                 265                 270

Gln Thr Glu Trp Lys Gln Ile Leu Asp Asn Thr Glu Val Lys Ala Val
        275                 280                 285

Ile Leu Gly Gly Asp Pro Ser Ser Gly Ala Arg Val Val Thr Gly Lys
    290                 295                 300

Val Asp Met Val Glu Asp Leu Ile Gln Glu Gly Ser Arg Phe Thr Ala
305                 310                 315                 320

Asp His Pro Gly Leu Pro Ile Ser Tyr Thr Thr Ser Phe Leu Arg Asp
                325                 330                 335

Asn Val Val Ala Thr Phe Gln Asn Ser Thr Asp Tyr Val Glu Thr Lys
            340                 345                 350

Val Thr Ala Tyr Arg Asn Gly Asp Leu Leu Leu Asp His Ser Gly Ala
        355                 360                 365

Tyr Val Ala Gln Tyr Tyr Ile Thr Trp Asp Glu Leu Ser Tyr Asp His
    370                 375                 380

Gln Gly Lys Glu Val Leu Thr Pro Lys Ala Trp Asp Arg Asn Gly Gln
385                 390                 395                 400

Asp Leu Thr Ala His Phe Thr Thr Ser Ile Pro Leu Lys Gly Asn Val
                405                 410                 415

Arg Asn Leu Ser Val Lys Ile Arg Glu Cys Thr Gly Leu Ala Trp Glu
            420                 425                 430

Trp Trp Arg Thr Val Tyr Glu Lys Thr Asp Leu Pro Leu Val Arg Lys
        435                 440                 445

Arg Thr Ile Ser Ile Trp Gly Thr Thr Leu Tyr Pro Gln Val Glu Asp
    450                 455                 460

Lys Val Glu Asn Asp
465

<210> SEQ ID NO 43
<211> LENGTH: 471
<212> TYPE: PRT
<213> ORGANISM: Streptococcus pneumoniae

<400> SEQUENCE: 43

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95
```

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Cys Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
    370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415

Asn Val Arg Asn Leu Ser Val Lys Ile Arg Glu Cys Thr Gly Leu Ala
            420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 44
<211> LENGTH: 471
<212> TYPE: PRT
<213> ORGANISM: Streptococcus pneumoniae

<400> SEQUENCE: 44

-continued

```
Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Cys Asn Asp Ser Arg Leu Tyr Pro Gly Ala Leu Leu Val Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
                100                 105                 110

Leu Gln Val Glu Asp Pro Ser Asn Ser Ser Val Arg Gly Ala Val Asn
            115                 120                 125

Asp Leu Leu Ala Lys Trp His Gln Asp Tyr Gly Gln Val Asn Asn Val
        130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Cys Gly Asp Pro Ser Ser Gly Ala Arg Val Val Thr
        290                 295                 300

Gly Lys Val Asp Met Val Glu Asp Leu Ile Gln Gly Ser Arg Phe
305                 310                 315                 320

Thr Ala Asp His Pro Gly Leu Pro Ile Ser Tyr Thr Thr Ser Phe Leu
                325                 330                 335

Arg Asp Asn Val Val Ala Thr Phe Gln Asn Ser Thr Asp Tyr Val Glu
            340                 345                 350

Thr Lys Val Thr Ala Tyr Arg Asn Gly Asp Leu Leu Leu Asp His Ser
        355                 360                 365

Gly Ala Tyr Val Ala Gln Tyr Tyr Ile Thr Trp Asp Glu Leu Ser Tyr
370                 375                 380

Asp His Gln Gly Lys Glu Val Leu Thr Pro Lys Ala Trp Asp Arg Asn
385                 390                 395                 400

Gly Gln Asp Leu Thr Ala His Phe Thr Thr Ser Ile Pro Leu Lys Gly
                405                 410                 415
```

Asn Val Arg Asn Leu Ser Val Lys Ile Arg Glu Ala Thr Gly Leu Ala
        420                 425                 430

Trp Glu Trp Trp Arg Thr Val Tyr Glu Lys Thr Asp Leu Pro Leu Val
        435                 440                 445

Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 45
<211> LENGTH: 30
<212> TYPE: DNA
<213> ORGANISM: Streptococcus pneumoniae

<400> SEQUENCE: 45
catgccatgg caaataaagc agtaaatgac                                        30

<210> SEQ ID NO 46
<211> LENGTH: 36
<212> TYPE: DNA
<213> ORGANISM: Streptococcus pneumoniae

<400> SEQUENCE: 46
cagccgctcg agctagtcat tttctacctt atcctc                                 36

<210> SEQ ID NO 47
<211> LENGTH: 30
<212> TYPE: DNA
<213> ORGANISM: Streptococcus pneumoniae

<400> SEQUENCE: 47
gaaggagata tcatatggca aataaagcag                                        30

<210> SEQ ID NO 48
<211> LENGTH: 22
<212> TYPE: DNA
<213> ORGANISM: Streptococcus pneumoniae

<400> SEQUENCE: 48
cctttcgggc tttgttagca gc                                                22

<210> SEQ ID NO 49
<211> LENGTH: 20
<212> TYPE: DNA
<213> ORGANISM: Streptococcus pneumoniae

<400> SEQUENCE: 49
taatacgact cactataggg                                                   20

<210> SEQ ID NO 50
<211> LENGTH: 19
<212> TYPE: DNA
<213> ORGANISM: Streptococcus pneumoniae

<400> SEQUENCE: 50
gctagttatt gctcagcgg                                                    19

<210> SEQ ID NO 51
<211> LENGTH: 20
<212> TYPE: DNA
<213> ORGANISM: Streptococcus pneumoniae

<400> SEQUENCE: 51

-continued

```
ctgcttttga agctttgata                                                20

<210> SEQ ID NO 52
<211> LENGTH: 20
<212> TYPE: DNA
<213> ORGANISM: Streptococcus pneumoniae

<400> SEQUENCE: 52
aggcttggga cagaaatggg                                                20

<210> SEQ ID NO 53
<211> LENGTH: 20
<212> TYPE: DNA
<213> ORGANISM: Streptococcus pneumoniae

<400> SEQUENCE: 53
ttgaaaggtc gcaactacat                                                20

<210> SEQ ID NO 54
<211> LENGTH: 20
<212> TYPE: DNA
<213> ORGANISM: Streptococcus pneumoniae

<400> SEQUENCE: 54
aaacacatct cctggatttt                                                20

<210> SEQ ID NO 55
<211> LENGTH: 20
<212> TYPE: DNA
<213> ORGANISM: Streptococcus pneumoniae

<400> SEQUENCE: 55
actacgagaa gtgctccagg                                                20
```

MODIFIED *STREPTOCOCCUS* PNEUMONIA PNEUMOLYSIN (PLY) POLYPEPTIDES

CROSS-REFERENCE TO RELATED APPLICATIONS

This application is a continuation application of U.S. Ser. No. 13/140,894, now U.S. Pat. No. 8,758,766, which was filed under 35 U.S.C. §371 and claims priority to International Application No. PCT/CA2009/001843, filed Dec. 22, 2009, which claims priority to U.S. provisional application 61/140,804 filed Dec. 24, 2008. These applications are incorporated herein by reference in their entirety.

TECHNICAL FIELD

This disclosure relates to immunogenic compositions comprising modified *Streptococcus pneumoniae* pneumolysin (PLY) polypeptides. Nucleic acids, polypeptides encoded thereby, compositions containing the same, methods for using such nucleic acids, polypeptides and compositions are also provided.

BACKGROUND

*Streptococcus pneumoniae* is an important pathogen, causing invasive diseases such as pneumonia, meningitis, and bacteraemia. Even in regions where effective antibiotic therapy is freely available, the mortality rate from pneumococcal pneumonia can be as high as 19% in hospitalized patients. In developing countries, in excess of three million children under the age of five years die each year from pneumonia, of which *S. pneumoniae* is the most commonly identified causative agent. *S. pneumoniae* also causes less serious, but highly prevalent infections such as otitis media and sinusitis, which have a significant impact on health-care costs in developed countries. Otitis media is especially important in young children, while sinusitis affects both children and adults.

Currently, licensed anti-pneumococcal vaccines are based on formulations of various capsular polysaccharide antigens derived from highly prevalent strains. Serotypes that most commonly cause invasive pneumococcal infection appear to differ somewhat in various regions of the world. In North America in the pre-vaccination era, serotypes 4, 6B, 9V, 14, 18C, 19F and 23F were the seven most common serotypes causing invasive disease in children aged ≤5 years of age (Butler, et al. *J. Infect. Dis.* 171 (4): 855-889 (1995)). These serotypes were reported to be responsible for 70-88% of invasive disease in these children and accounted for 100% of *S. pneumoniae* with high-level penicillin-resistance.

Two types of pneumococcal vaccines are in clinical use: the 23-valent Pneumococcal Polysaccharide Vaccine (23-PPV) and the 7-valent Pneumococcal Conjugate Vaccine (PCV7) (Siber, et al. Pneumococcal Vaccines: The Impact of Conjugate Vaccine. Washington D.C.: ASM Press; 2008). The polysaccharide antigens in 23-PPV elicit a T-cell-independent immune response, resulting in poor immunologic memory. Additionally, while 23-PPV confers 60-80% protection against invasive pneumococcal disease (IPD) in adults and the elderly, immunity wanes substantially after 5 years and it is poorly immunogenic in children ≤2 years of age. Robust T-cell responses with immunologic memory is observed in young children vaccinated with PCV7 (Prevnar®, Wyeth Pharmaceuticals, Inc.) Prevnar 13 (PCV13), which includes the serotypes of PCV7 and serotypes 1, 3, 5, 6A, 7F, and 19A was recently recommended for approval by a Food and Drug Administration advisory committee on vaccines and related biological products. Studies are also underway on a ten-valent vaccine (Synflorix, GSK) containing polysaccharides of ten pneumococcal serotypes (1, 4, 5, 6B, 7F, 9V, 14, 18C, 19F, and 23F) conjugated to a carrier protein.

Despite their resounding success and significant public health impact, anti-pneumococcal conjugate vaccines have also had some well known shortcomings, including the complexity of conjugate vaccine production, which increases manufacturing costs. More important, however, is the finding that polysaccharide-based conjugate vaccines protect only against infections caused by bacteria that express the particular capsule-type represented by the vaccine. This is a problem in regions such as Latin America, Asia and Africa, in which the serotypes represented by PCV7 are responsible for much less invasive disease than elsewhere in the world (Black, et al. In: Plotkin S A, et al. eds. Vaccines, 5th Edition. WB Saunders. Chapter 23 (2008); Garcia, et al. *Rev. Panam. Salud. Publica.* 19(5):340-8 (2006); Lagos, R. *Pediatr. Infect. Dis. J.* 21 (12): 1115-23 (2002)). This need may be addressed by the new generation of conjugate vaccines, the 10- and 13-valent PCV vaccines (PCV-10 and PCV-13), currently in development and/or licensure stage.

Regional issues (e.g., limited serotype coverage, the potential for replacement disease with non-vaccine serotypes, capsular switching, carrier-induced suppression, and manufacturing and supply constraints are understood by those of skill in the art to present significant problems in vaccinating worldwide populations. It is known that *S. pneumoniae* is antigenically and clonally diverse (Hanage, et al. *Infect. Immun.* 73(1):431-5 (2005)), with a single pneumococcal serotype typically including a number of genetically divergent clones. Pneumococcal proteins are known to be much more conserved between serotypes and have thus been considered as potential vaccines.

Pneumolysin has been reported to be an intracellular protein that causes a variety of toxic effects in vivo when released upon lysis of pneumococci. The protein is highly conserved in both amino acid sequence and antigenicity among clinical isolates, thus satisfying some basic criteria for its use as a vaccine antigen (Paton, et al. *Infect. Immun.* 40(2) 548-52 (1983); Lock, et al. *Microb. Pathog.* 5(6): 461-67 (1988)). However, it has inherent hemolytic properties, and mutants have therefore been developed and studied for their potential as vaccines. Historically the most commonly studied pneumolysin mutant is PdB, containing a single amino acid change, Trp433Phe (Paton, et al. *Infect. Immun.* 59(7):2297-304 (1991); Lu, et al. *Infect. Immun.* 77(5): 2076-83 (2009); Ogunniyi, et al. *Infect Immun.* 75(1):350-7 (2007); Berry, et al. *Infect. Immun.* 63(5): 1969-74 (1995); Berry, et al. *Infect. Immun.* 67(2): 981-85 (1999)).

Other PLY mutants, including ΔAla146 with a deletion of amino acid 146, and ΔAla146R147, have been recently described (Kirkham, et al. *Infect. Immun.* 74(1): 586-93 (2006)). Both ΔAla146 and ΔAla146R147 were shown to lack haemolytic activity against human erythrocytes. Alum-adjuvanted ΔAla146 was also shown to be as protective as alum-adjuvanted wild-type PLY.

Although there were differences in the mouse strains used, the *S. pneumoniae* serotypes used and the routes of immunization, compilation of results from these studies using sepsis models have indicated that PdB or ΔAla146 prolong survival of mice when compared with placebo control groups. In the pneumonia model, immunization of mice with PdB yielded a significant decrease in numbers of pneumococci in the lungs of infected mice compared to a placebo control (Briles, et al. *J. Infect. Dis.* 188(3): 339-48 (2003)). Moreover, in most of these findings, PdB was found to provide a superior protection against a wide variety of strains when used in combination with other virulence factors such as PspA, PspC or PsaA (Lu, supra; Ogunniyi, supra; Berry (1995), supra). Although the PdB mutant provided significant protection in some models, it had the drawback of possessing residual hemolytic activity. However, as mentioned above, ΔAla146 provided both protective immunity and a lack of haemolytic activity.

While several mutant PLY vaccines have been developed, there is a clear need in the art for additional mutants that are both protective and lack haemolytic activity. One such mutant, PlyD1, is described herein. The data presented herein shows that PlyD1 lacks hemolytic activity, generates neutralizing antibodies that inhibit hemolysis by PLY in vitro, and is protective in certain animal models.

BRIEF DESCRIPTION OF THE FIGURES

FIG. 1. Exemplary PLY amino acid sequences—alleles and modifications.
FIG. 2. In vitro hemolytic activity, toxin mediated lysis of sheep red blood cells, of mutations at position 293.

SUMMARY OF THE DISCLOSURE

Figure 3:
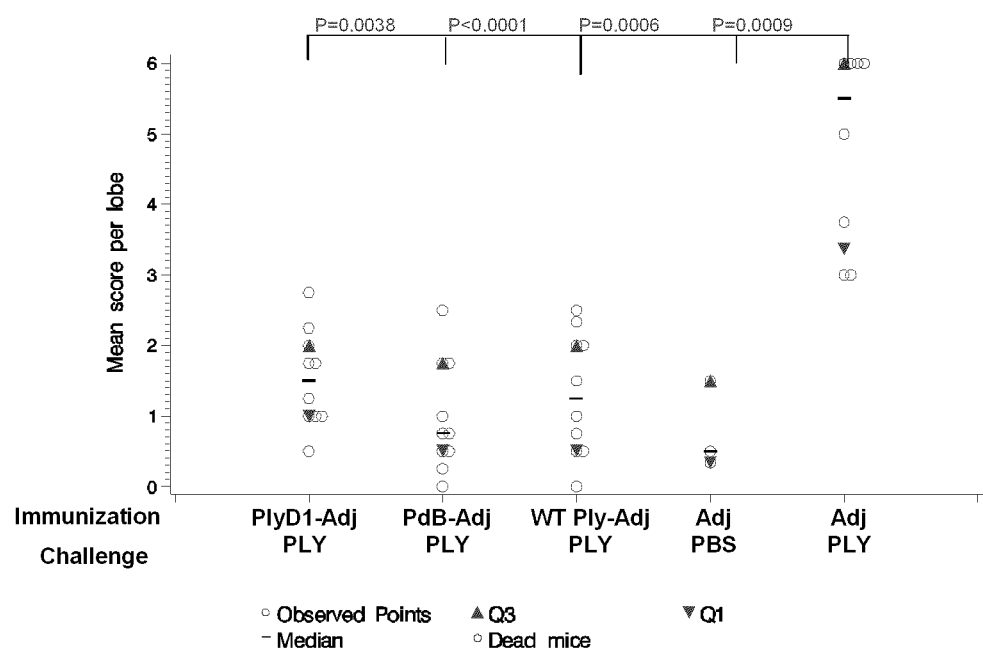
FIG. 3. Decreased lung tissue damage mediated by PLY following immunization with mPLY.

This disclosure relates to modified *Streptococcus pneumoniae* pneumolysin proteins ("mPLY") or fragments thereof which can be used as immunogens in an immunogenic composition or vaccine against invasive pneumococcal disease caused by *S. pneumoniae*. The mPLY typically include at least one amino acid difference from wild-type PLY ("wtPLY"; e.g., any of SEQ ID NOS.:2-42). Upon administration of mPLY to a host, mPLY induces the production of anti-wtPLY and/or anti-mPLY antibodies, which may include antibodies that prevent and/or inhibit the hemolytic activity of wtPLY and/or protective antibodies against organisms expressing wtPLY. Preferably, mPLY induces antibodies reactive with wtPLY and exhibits decreased hemolytic activity (including none) against erythrocytes as compared to wtPLY. In some embodiments, wtPLY is modified at one or more of amino acid 65 (threonine, "Thr65"), amino acid 293 (glycine, "Gly293"), and/or 428 (cysteine, "Cys428") to any other amino acid. In certain embodiments, wtPLY is modified at Gly293 and one or more additional amino acids such as, but not limited to, Thr65 and/or Cys428. In certain embodiments, Thr65 is substituted by cysteine, Gly293 is substituted by cysteine, and/or Cys428 is substituted by alanine. Also provided are nucleic acids encoding mPLY, methods for making mPLY, methods for immunizing, protecting, treating, and/or preventing hosts from infection or infected by organisms expressing wtPLY, and compositions for doing the same. Other embodiments will be clear from the descriptions provided herein.

DETAILED DESCRIPTION

Provided herein are modified pneumolysin (PLY) polypeptides and fragments thereof, immunogenic compositions, and vaccines comprising such polypeptides and/or fragments (e.g., peptides), methods of preparing such polypeptides and/or fragments, and methods of using such polypeptides and/or fragments. A modified PLY polypeptide ("mPLY") and/or fragment of mPLY is one having differences in nucleic acid or amino acid sequence as compared to a wtPLY sequence. A mPLY polypeptide typically, but not necessarily, has at least one modified amino acid sequence as compared with a wtPLY and/or fragment thereof. The modification is typically an amino acid substitution, insertion, and/or deletion. The mPLY polypeptide and/or fragment thereof may be preferably substantially nontoxic when compared to a protein substantially corresponding to a wtPLY protein at the same dose. Preferably, the modified sequences provide for changes in certain activities of mPLY that are typically associated with wtPLY, especially undesirable activities including but not limited to membrane permeation, cell lysis, and cytolytic activity against human erythrocytes and other cells (a "cell" may be human and/or non-human). It is also preferred that mPLY retain the ability to induce anti-PLY (including but not limited to anti-wtPLY) protective and/or neutralizing antibodies following administration to a host (e.g., an animal such as a mammal, e.g., human being). In certain embodiments, such antibodies reduce (including eliminate) the hemolytic activity of wtPLY, and/or lung tissue toxicity, and/or bind to microorganisms expressing wtPLY, and/or bind to wtPLY per se, and/or provide protection against infection or dissemination of disease caused by microorganisms expressing wtPLY (e.g., *Streptococcus pneumoniae*).

The wtPLY sequence may be any PLY expressed in an organism, including but not limited to a microorganism pathogenic (e.g., "causing disease") in a higher organism (e.g, an animal such as a mammal, e.g., human being). An exemplary pathogenic organism is *Streptococcus pneumoniae*. Wild-type PLY polypeptides are typically encoded by a ply gene, which are highly conserved genes but do exhibit some variation (e.g., Walker, et al. *Infect. Immun.* 55: 1184-1187 (1987); Mitchell, et al. *Nucleic Acid Res.* 18: 4010 (1990); Jefferies, et al. *J Infect Dis.* 196(6):936-44 (2007)). A PLY structural model was constructed based on sequence similarity with perfringolysin O and homology modeling using the Discovery Studio suite of programs available from Accelrys Software, Inc. The model indicates that the wt-PLY is ~20% α-helix and ~40% β-sheet with four distinct structural domains: D1 (residues 6-21, 58-147, 198-243, 319-342), D2 (residues 22-57, 343-359), D3 (residues 148-197, 244-318), and D4 (residues 360-469). Wild-type PLY may be modified in any one or more of D1, D2, D3, or D4. Exemplary wtPLY amino acid sequences include but are not limited to those shown in any of Walker, et al. (supra), Mitchell, et al. (supra), Jeffries, et al. (supra), FIG. 1, SEQ ID NOS.: 2-42, GenBank Accession Nos. M17717, EF413923, EF413924, EF413925, EF413926, EF413927, EF413928, EF413929, EF413930, EF413931, EF413932, EF413933, EF413934, EF413935, EF413936, EF413937, EF413938, EF413939, EF413940, EF413941, EF413942, EF413943, EF413944, EF413945, EF413946, EF413947, EF413948, EF413949, EF413950, EF413951, EF413952, EF413953, EF413954, EF413955, EF413956, EF413957, EF413958, EF413959, and/or EF413960. It is noted that any of the variations between these sequences may be combined with any other variations found within such wtPLY (which may include synthetic modifications described herein or elsewhere) to generate additional wtPLY that may be modified to generate mPLY. Such wtPLY polypeptides typically, but not necessarily, share at least about (referring to each of the following values independently) 90%, 95%, or 99% sequence identity with the wtPLY amino acid sequence shown in SEQ ID NO.:2 as determined using mafft (Kato, et al. Nucleic Acids Res. 30: 3059-3066 (2002); Kato, et al. Brief Bioinform. 9: 286-294

(2008)). In certain embodiments, a wtPLY may share 98.8% sequence identity with the wtPLY sequence shown in SEQ ID NO.:2 as determined using mafft. The modifications introduced into wtPLY to produce mPLY may be made to any polypeptide sharing identity with wild-type PLY, including those polypeptides having about 90%, 95%, 98%, 99%, or 99.9% identify with SEQ ID NO.:2. Any differences in the amino acid sequence of wtPLY polypeptides are typically but not necessarily phenotypically silent. It should be noted that the wtPLY listed herein are only exemplary; other suitable wtPLY sequences are known in the art and would be suitable to modification as described herein.

Exemplary mPLY polypeptides contain, for example, wtPLY modified at amino acids threonine 65 ("Thr65"), glycine 293 ("Gly293"), and/or cysteine 428 ("Cys428"). A modification of any of these amino acids may be referred to using conventional nomenclature, e.g., by indicating the amino acid being modified and the modification made thereto (e.g., Thr65X, Gly293X, Cys428X, where X typically indicates the substituted amino acid, or a deletion of that amino acid). In one embodiment, wtPLY is modified at Thr65 to cysteine ("Ply-T65C"). In another embodiment, wtPLY is modified at glycine 293 to alanine ("Ply-G293A"), cysteine ("Ply-G293C"), valine ("Ply-G293V"), or threonine ("Ply-G293T"). In another embodiment, wtPLY is modified at Cys428 to alanine ("Ply-Cys428A"). In other embodiments, wtPLY is modified at Gly293 and one or more additional amino acids such as, but not limited to, Thr65 and/or Cys428. In other embodiments, wtPLY is modified at Thr65 and one or more additional amino acids such as, but not limited to, Gly293 and/or Cys428. In other embodiments, wtPLY is modified at Cys428 and one or more additional amino acids such as, but not limited to, Thr65 and/or Gly293. Modifications at Thr65, Gly293, and/or Cys428 may be made to any wtPLY to produce mPLY polypeptides. Preferred substitutions in each of these embodiments is cysteine for Thr65; cysteine, valine, or threonine for Gly293; and/or alanine for Cys428. Exemplary mPLY polypeptides are shown in SEQ ID NOS. 43 and 44. Any of these modifications may be introduced into any wtPLY described herein or elsewhere combined with any other modifications to produce mPLY polypeptides using standard molecular biology and biochemical techniques.

PLY (wtPLY or mPLY) activity may be assayed and characterized by methods known to those of skill in the art (e.g., Paton, et al., supra; Nato, et al. *Infect Immun.* 59(12):4641-4646 (1991)). Any one or more of the assays described herein, or any other one or more suitable assays, may be used to determine the suitability of mPLY as a vaccine. Two suitable, exemplary assays are the in vitro hemolytic assay and the hemolysis inhibition assay. The in vitro hemolysis assay measures the hemolytic (e.g., cytolytic) activity of mPLY relative to wtPLY. The hemolysis inhibition assay measures the ability of antisera raised against mPLY to inhibit hemolysis by PLY, and (typically) comparing anti-mPLY antisera to anti-wtPLY antisera. Either or both of these assays may be utilized to determine the activity of a particular mPLY. In vivo assays may also be used, including but not limited to the sepsis model, the focal pneumonia model, and the intranasal challenge models essentially as described in Example 8. Thus, a suitable mPLY may be one that exhibits lower hemolytic activity than wtPLY (e.g., via an in vitro hemolysis assay). A suitable mPLY may also be one that, following administration to a host, causes the host to produce antibodies that inhibit hemolysis by wtPLY (e.g., via a hemolysis inhibition assay), is immunogenic (e.g., an immunogenic composition, one that induces the production of antibodies or a cytotoxic T cell response against wtPLY or microorganisms expressing wtPLY), protective (e.g., a prophylactic or therapeutic vaccine composition, one that induces an immune response that protects the host against infection by or limits an already-existing infection, respectively, by an organism expressing wtPLY), provides benefits as measured by any one or more of the in vivo assays described herein (e.g., sepsis model, focal pneumoniae model, intranasal challenge, lung damage assay), and/or increases or decreases expression of cytokines by macrophages as compared to wtPLY. It is to be understood that these methods for identifying and/or characterizing mPLY are exemplary and non-limiting; other assays may also be suitable.

In the in vitro hemolysis assay, test polypeptides (e.g., wtPLY, mPLY) may be separately serially diluted across a plastic microtiter plate in serial dilutions (e.g., 2-fold) with a highest concentration typically being about 0.5 mg/mL of test polypeptide. Bovine serum albumin (BSA) may be included to prevent adsorptive losses on the plastic microtiter plate. Sheep red blood cells may then be added to all wells, and the plates incubated for a sufficient period of time (e.g., 30 min.). Positive controls (e.g., 100% lysis measurement is obtained by the addition of 1% Trition X-100 to particular wells) and negative controls (e.g., PBS alone) are typically included. The plate may then be centrifuged to separate the intact cells from the lysed cells. The supernatant containing the lysed cells may then be transferred to a fresh plate and subjected to an $A_{540}$ hemoglobin release assay (lysed cells release hemoglobin). The specific activity may be determined as the inverse of protein concentration (mg/mL) at which 50% hemolysis occurred relative to the positive control. Using this assay system, it is preferred that a particular mPLY have a specific activity of less than wtPLY. For example, mPLT may have a specific activity of about 0%, 0.0005%, 0.001%, 0.005%, 0.01%, 0.05%, 0.1%, 0.5%, 1%, 5% or <10% the specific activity of wtPLY. A specific activity of approximately within these ranges typically indicates the particular mPLY is within acceptable parameters.

In the hemolysis inhibition assay, anti-PLY (wtPLY or mPLY) antisera is produced essentially as described in the art or herein and serially diluted (e.g., two-fold) across a microtiter plate (e.g., a 96-well plate) and a constant amount of wtPLY is added to each well to be analyzed. Sheep red blood cells are added to all wells and the assay proceeds as per the in vitro hemolysis assay described in the preceding paragraph. The data are plotted as percent hemolysis versus antiserum titer (log scale). The 50% hemolysis inhibition titer is taken as the inverse of the serum dilution at which the percent hemolysis is reduced to 50%. Using this assay system, it is preferred that a particular mPLY have a similar (e.g., anywhere from about 75 to about 100%) or higher 50% hemolysis inhibition titer than wtPLY. For example, it is preferred that a particular mPLY induce an antisera having a 50% hemolysis inhibition titer (using serial two-fold dilutions) of about 1:16, 1:32, 1:64, 1:128, 1:256, 1:512, 1:1024, 1:2048, 1:5096, or 1:10,192, or greater. A 50% hemolysis inhibition titer of approximately within these ranges typically indicates the particular mPLY is within acceptable parameters.

In certain embodiments, it may be desired that the mPLY have both an acceptable specific activity as determined by the in vitro hemolysis assay and an acceptable 50% hemolysis inhibition titer. For instance, a suitable mPLY may have a specific activity (as determined using the in vitro hemolysis assay) of about (referring to each of the following values independently) 0%, 0.0005%, 0.001%, 0.005%, 0.01%, 0.05%, 0.1%, 0.5%, 1%, 5% or <10% the specific activity of wtPLY, and a 50% hemolysis inhibition titer (using serial two-fold dilutions) of about 1:128, 1:256, 1:512, 1:1024, 1:2048, 1:5096, or 1:10,192.

wtPLY is known to activate macrophages to generate cytokines (Malley, et al. PNAS USA, 100(4):1966-71 (2003)). Suitable mPLY may be identified by determining macrophage activation by measuring mPly-induced cytokine production (e.g., (IL-1β, IL-6 and IL-10) in vitro. Macrophage-like cells (e.g., human MM6 and mouse J774A.1 cells) may be incubated overnight with wtPLY or mPLY, and treated or not treated with proteinase K and heat (to distinguish false positives due to lipopolysaccharide (LPS) contamination in the treated group). Cytokine production (e.g., IL-6, IL-10, TNF-α, IL-1β) may be measured by ELISA after overnight incubation. In certain embodiments, a suitable mPLY will induce expression of cytokines (e.g., IL-1β, IL-6 and IL-10) more than will wtPLY. In other embodiments, a suitable mPLY will induce expression of cytokines (e.g., IL-1β, IL-6 and IL-10) less than will wtPLY. The difference in the levels of expression induced by mPLY and wtPLY may be, for instance, about 10, 20, 30, 40, 50, 60, 70, 80, 90, 100% or more than 100%.

It is also desired that antibodies generated against mPLY provide for lower levels of lung tissue damage induced by wtPLY or organisms expressing wtPLY. To test the effectiveness of such antibodies using animal models, one or more mice (or other suitable model animal) may be immunized with mPLY (e.g., a dose of about 1, 2, 5 or 10 μg for a sufficient period of time), and then challenged with wtPLY (e.g., a dose of about 1, 2, 5, or 10 μg for a sufficient period of time) or an organism expressing wtPLY. After a sufficient period of time (e.g., a period of hours, days, weeks), the lungs may be harvested and stained to observe tissue damage. wtPLY typically causes perivascular edema, thickened, disrupted alveolar walls, diminished alveolar space, and fluid and blood infiltration of the alveolar spaces. In certain embodiments, a suitable mPLY may induce antibodies that reduce lung damage by, for instance, about 10, 20, 30, 40, 50, 60, 70, 80, 90, or 100% as compared to that induced by wtPLY or an organism expressing wtPLY.

In addition, in certain embodiments, it is preferred that a suitable mPLY exhibit immunogenic properties (e.g., inducing a neutralizing and/or protective immune response following administration to a host). The presence of neutralizing and/or protective immune response may be demonstrated by demonstrating that infection by organisms expressing wtPLY is decreased in immunized individuals (e.g., human beings, or using animal models). Suitable animal models include the sepsis model, the focal pneumoniae model, and the intranasal challenge model. In the sepsis model, test animals (e.g., mice or similar model) may be immunized (e.g., subcutaneously, intravenously, intramuscularly, intradermally, intranodally, intranasally) with mPLY (with or without one or more adjuvants at suitable timepoints such as days 0, 7, 14, 21, 28, 35, 42), and then after a suitable amount of time (e.g., about 1, 2, 3, 4, 5, 6, 7, 8, 9, or 10 weeks) challenged by intranasal (IN) injection with a suitable amount of wt-PLY expressing organism (e.g., $10^7$ colony forming units (cfu) of S. pneumoniae serotype 6B). Following the challenge, mice may be monitored for mortality, and sample bleeds may be drawn. Sera may be analyzed for total PLY-specific IgG response using, for example, an antibody ELISA and for PLY neutralizing capacity using, for example, an inhibition of hemolysis assay. Statistical analysis (e.g., Fisher's exact test, Wilcoxon test, Mann-Whitney Test) may then be performed on the survival and ELISA/inhibition of hemolysis assay data to determine whether the mPLY is effective.

mPlyD1 may also be tested using a focal pneumonia mouse model. Briefly, animals may be immunized (e.g., subcutaneously, intravenously, intramuscularly, intradermally, intranodally, intranasally) with a purified recombinant PlyD1 protein with or without adjuvant. Test animals (e.g., mice or similar model) may be immunized with mPLY (with or without one or more adjuvants at suitable timepoints such as days 0, 7, 14, 21, 28, 35, 42), and then after a suitable amount of time (e.g., about 1, 2, 3, 4, 5, 6, 7, 8, 9, or 10 weeks) challenged by intranasally (IN) with a suitable amount of wt-PLY expressing organism (e.g., $3$-$7 \times 10^6$ cfu of S. pneumoniae strain EF3030 (serotype 19F)). Following the challenge, mice may be monitored for mortality, and sample bleeds may be drawn. Sera may be analyzed for total PLY-specific IgG response using, for example, an antibody ELISA and for PLY neutralizing capacity using, for example, an inhibition of hemolysis assay. Statistical analysis (e.g., Fisher's exact test, Wilcoxon test, Mann-Whitney Test) may then be performed on the survival and ELISA/inhibition of hemolysis assay data to determine whether the mPLY is effective.

The effectiveness of mPlyD1 as a vaccine may also be evaluated in-house using an intranasal challenge mouse model. In this model, mice may be immunized (e.g., subcutaneously, intravenously, intramuscularly, intradermally, intranodally, intranasally) with purified recombinant PlyD1 proteins at an effective dose (e.g., from about 0.25 to 25 μg) with or without one or more adjuvants at suitable timepoints such as days 0, 7, 14, 21, 28, 35, 42), and then after a suitable amount of time (e.g., about 1, 2, 3, 4, 5, 6, 7, 8, 9, or 10 weeks) challenged by intranasally (IN) with a suitable amount of wt-PLY expressing organism (e.g., a lethal dose ($5 \times 10^5$ cfu) of S. pneumoniae strain 14453 (serotype 6B)). Following the challenge, mice may be monitored for mortality, and sample bleeds may be drawn. Sera may be analyzed for total PLY-specific IgG response using, for example, an antibody ELISA and for PLY neutralizing capacity using, for example, an inhibition of hemolysis assay. Statistical analysis (e.g., Fisher's exact test, Wilcoxon test, Mann-Whitney Test) may then be performed on the survival and ELISA/inhibition of hemolysis assay data to determine whether the mPLY is effective.

Immunogenic compositions and vaccines containing mPLY polypeptides and/or fragments thereof may be used to treat diseases such as, for example, invasive pneumococcal such as pneumonia, meningitis, otitis media, and bacteremia. The polypeptides and fragments exhibit substantially reduced toxicity compared to the native toxin. Nucleic acid sequences encoding the mPLY polypeptides and/or fragments, vectors containing such nucleic acid sequences, and host cells capable of expressing the mutant PLY polypeptides and/or fragments are also provided. The mPLY polypeptides and/or fragments preferably exhibit decreased toxicity relative to wtPLY (e.g., lower hemolytic/cytolytic activity) and elicit neutralizing antibodies which are cross-reactive with antibodies elicited by the wtPLY. mPLY polypeptides and/or fragments may be used to produce immunological compositions which may include vaccines. An immunological composition is one that, upon administration to a host (e.g., an animal), induces or enhances an immune response directed against the antigen or immunogen contained within the composition. This response may include the generation of antibodies (e.g, through the stimulation of B cells) or a T cell-based response (e.g., a cytolytic response). These responses may or may not be protective or neutralizing. A protective or neutralizing immune response is one that is detrimental to the infectious organism corresponding to the antigen (e.g, from which the antigen was derived) and beneficial to the host (e.g., by reducing or preventing infection). As used herein, protective or neutralizing antibodies and/or cellular responses may be reactive to mPLY, wtPLY, or fragments thereof and reduce or inhibit the lethality of wtPLY (or organisms expressing wtPLY or mPLY) when tested in animals. An immunological composition that, upon administration to a host, results in a protective or neutralizing immune response, may be considered a vaccine. Immunological compositions comprising one or more mPLY polypeptides may also include one or more additional antigens, such as one or more antigens of *S. pneumoniae*. Exemplary antigens include, for example, PcPA and/or PhtD. Other variations of immunological compositions are also contemplated as would be understood by one of skill in the art.

As mentioned above, mPLY polypeptides and/or fragments thereof typically have at least one nucleic acid and/or one amino acid substitution. Modified polypeptides may also exhibit at least one change in a biological function (e.g., immunogenicity, haemolytic activity) compared with a wtPLY. mPLY polypeptides or fragments thereof are preferably substantially nontoxic when compared to a wtPLY protein at the same dose, elicit antibodies that are preferably protective or neutralizing and cross-reactive with antibodies elicited by a wtPLY protein. A mPLY polypeptide and/or fragment thereof may be generated using a variety of methods including, but not limited to, site-directed mutagenesis, random mutagenesis, conventional mutagenesis, in vitro mutagenesis, spontaneous mutagenesis and chemical synthesis. Methods of mutagenesis can be found in Sambrook et al., A Guide to Molecular Cloning, Cold Spring Harbour, N.Y. (1989) and Sambrook and Russel. Molecular Cloning: A Laboratory Manual (2001), for instance.

This disclosure further relates to antibodies, preferably protective or neutralizing antibodies, generated using a mPLY polypeptide or fragment thereof where the resultant antibodies are reactive to wtPLY and/or fragments thereof. Also provided are methods for eliciting the production of antibodies, which may be protective and/or neutralizing, reactive to the mPLY or fragments thereof. The antibodies may elicit both active and passive immunity. The mPLY polypeptides and/or fragments thereof may also be used to identify and isolate antibodies, which may be protective and/or neutralizing, that are cross-reactive with those elicited by wtPLY.

Nucleic acids encoding mPLY polypeptides are also provided. Also provided are variants of such sequences, including degenerate variants thereof. In certain embodiments, a nucleic acid molecule encoding the mPLY polypeptide and/or fragment may be inserted into one or more expression vectors, as discussed below in greater detail. In such embodiments, the mPLY polypeptide and/or fragment is/are encoded by nucleotides corresponding to the amino acid sequence. The particular combinations of nucleotides that encode the various amino acids are well known in the art, as described in various references used by those skilled in the art (i.e., Lewin, B. *Genes V*, Oxford University Press, 1994), and as shown in Table 1 below. Nucleic acid variants may use any combination of nucleotides that encode the polypeptide of interest.

TABLE 1

| Phe (F) | TTT | Ser (S) | TCT | Tyr (Y) | TAT | Cys (C) | TGT |
|---|---|---|---|---|---|---|---|
|  | TTC |  | TCC |  | TAC |  | TGC |
| Leu (L) | TTA |  | TCA | TERM | TAA | TERM | TGA |
|  | TTG |  | TCG |  | TAG | Trp (W) | TGG |
|  | CTT | Pro (P) | CCT | His (H) | CAT | Arg (R) | CGT |
|  | CTC |  | CCC |  | CAC |  | CGC |

TABLE 1-continued

|  | CTA |  | CCA | Gln (Q) | CAA |  | CGA |
|---|---|---|---|---|---|---|---|
|  | CTG |  | CCG |  | CAG |  | CGG |
| Ile (I) | ATT | Thr (T) | ACT | Asn (N) | AAT | Ser (S) | AGT |
|  | ATC |  | ACC |  | AAC |  | AGC |
|  | ATA |  | ACA | Lys (K) | AAA | Arg (R) | AGA |
| Met (M) | ATG |  | ACG |  | AAG |  | AGG |
| Val (V) | GTT | Ala (A) | GCT | Asp (D) | GAT | Gly (G) | GGT |
|  | GTC |  | GCC |  | GAC |  | GGC |
|  | GTA |  | GCA | Glu (E) | GAA |  | GGA |
|  | GTG |  | GCG |  | GAG |  | GGG |

Modified PLY polypeptides and/or fragments are typically selected to include least one amino acid substitution, and optionally at least one change in a biological function compared with wtPLY. Modified PLY proteins or fragment thereof may be selected to ensure that they are substantially non-toxic when compared to a protein substantially corresponding to a wtPLY protein at the same dose and elicit neutralizing antibodies which may be cross-reactive with antibodies elicited by a wtPLY protein. As described herein, mPLY polypeptides and fragments thereof may be useful in immunogenic compositions or vaccines against invasive pneumococcal disease (e.g., pneumonia, meningitis, otitis media, bacteremia) caused by *Streptococcus pneumoniae*.

Amino acid substitution may be conservative or non-conservative. Substitutions that result in a structural change that may affect mPLY activity include the following:

1. change from one type of charge to another (e.g., arginine to glutamate);
2. change from charge to noncharged (e.g., glutamate to proline);
3. change in cysteine residues and formation of disulfide bonds (e.g., glutamate to cysteine and threonine to cysteine);
4. change from hydrophobic to hydrophilic residues (e.g., alanine to serine);
5. change from hydrophilic residues to hydrophobic residues (e.g., aspartate to leucine);
6. change in size of the amino acid (e.g., glycine to valine);
7. change to a conformationally restrictive amino acid or analog (e.g., glutamate to proline); and
8. change to a non-naturally occurring amino acid or analog.

Conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table 2.

TABLE 2

| Original Residues | Exemplary Conservative Substitutions | Preferred Conservative Substitution |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |

TABLE 2-continued

| Original Residues | Exemplary Conservative Substitutions | Preferred Conservative Substitution |
|---|---|---|
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The specific amino acid substitution selected may depend on the location of the site selected.

In certain embodiments, nucleic acids encoding mPLY polypeptides and/or fragments substituted may be selected based on the degeneracy of the genetic code. Where the nucleic acid is a recombinant DNA molecule useful for expressing a polypeptide in a cell (e.g., an expression vector), such a substation may result in the expression of a polypeptide with the same amino acid sequence as that originally encoded by the DNA molecule. As described above, however, substitutions may be conservative, or non-conservative, or any combination thereof.

A skilled artisan will be able to determine suitable variants of mPLY polypeptides and/or fragments provided herein using well-known techniques. For identifying suitable areas of the molecule that may be changed without destroying biological activity (i.e., pore-forming activity, red blood cell (RBC) agglutination, RBC hemolysis, MHC binding, immunogenicity), one skilled in the art may target areas not believed to be important for that activity. For example, when PLY derivatives with similar activities from the same species or from other species are known, one skilled in the art may compare the amino acid sequence of a polypeptide to such similar polypeptides. By performing such analyses, one can identify residues and portions of the molecules that are conserved. It will be appreciated that changes in areas of the molecule that are not conserved relative to such similar pneumolysin derivatives would be less likely to adversely affect the biological activity and/or structure of a polypeptide. Similarly, the residues required for binding to MHC are known, and may be mutated to improve binding of PLY antigenic sequences to MHC molecules. However, modifications resulting in decreased binding to MHC will not be appropriate in most situations. One skilled in the art would also know that, even in relatively conserved regions, one may substitute chemically similar amino acids for the naturally occurring residues while retaining the desired characteristics of the polypeptide and/or fragment. Therefore, even areas that may be important for biological activity or for structure may be subject to conservative amino acid substitutions without destroying the biological activity or without adversely affecting the structure of the mPLY derivative.

In other embodiments, the mPLY polypeptides and/or fragments described herein may include fusion polypeptide segments that assist in purification or detection of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 2 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strepavidin-derived tag peptide, a T7 tag peptide, a FLAG peptide, or other peptides that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage.

In certain embodiments, the mPLY polypeptides and/or fragments may be directly or indirectly (i.e., using an antibody) labeled or tagged in a manner which enables it to be detected. Labels include fluorochromes such as fluorescein, rhodamine, phycoerythrin, Europium and Texas Red, chromogenic dyes such as diaminobenzidine, radioisotopes, macromolecular colloidal particles or particulate material such as latex beads that are coloured, magnetic or paramagnetic, binding agents such as biotin and digoxigenin, and biologically or chemically active agents that can directly or indirectly cause detectable signals to be visually observed, electronically detected or otherwise recorded, for example in a FACS, ELISA, Western blot, TRFIA, immunohistochemistry, evanescence, Luminex bead array, or dipstick or other lateral flow assay format. Suitable antibody-binding molecules for use in such methods may include immunoglobulin-binding antibodies, for example anti-human Ig antibodies, anti-human Ig antibodies, anti-human antibodies specific for Ig isotypes or for subclasses of IgG, or specific for Staphylococcal protein A or G.

Preferred fluorescent tag proteins include those derived from the jelly fish protein known as green fluorescent protein (GFP). Further information on GFP and other fluorophores is given in the following publications: Tsien R Y, "The Green Fluorescent Protein" Annual Reviews of Biochemistry 1998; 67:509-544 Verkhusha, V and Lukyanov, K. "The Molecular Properties and Applications of Anthoza Fluorescent Proteins and Chromophores" Nature Biotechnology 2004; 22:289-296. Plasmid vectors encoding a wide range of fluorescent tag proteins are commercially available from various suppliers including an array of "Living Colours™ Fluorescent Proteins" available commercially from Clontech Laboratories, Inc. Similar vectors can also be obtained from other suppliers including Invitrogen and Amersham Biosciences. Suitable fluorescent proteins derived from GFP are the red-shifted variant EGFP, the cyan shifted variant ECFP and the yellow shifted variant EYFP. EGFP is preferred as the fluorescent marker because it gives bright fluorescence combined with minimal effect on the antigenic properties of the target antigen. Alternative fluorescent marker proteins are commercially available. Biologically or chemically active agents include enzymes, which catalyse reactions that develop or change colours or cause changes in electrical properties, for example, and may also be utilized. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples include horseradish peroxidase and chemiluminescence. In some embodiments, the non-immobilized, antibody-binding molecule, or polypeptide may be detected using an antibody which binds to said non-immobilised antibody-binding molecule or polypeptide. A suitable detection antibody may be labeled by means of fluorescence. The label may be a fluorescent marker (tag) which is used to label the target antigen directly such that the antigen and the fluorescent marker form a fusion protein.

If antibodies against the target antigen are present in a biological sample, the antigen may be labeled with the tag bound to those antibodies, and the complex formed thereby detected using immunoprecipitation. The fluorescence associated with the tag may then be used to determine that protein has been precipitated (qualitative determination) or to determine the amount of protein precipitated (quantitative determination). For example, soluble extracts of a fluorescence-tagged antigen may be incubated with patient sera for an appropriate period of time such as overnight at 4° C. (typically 10-15 µl of serum to 300-500 µl of extract or less) to allow antibodies to bind to the antigen. Protein A or Protein G Sepharose beads, preincubated with low IgG fetal calf serum (Sigma) to block non-specific binding, are then added to the extract/serum mix containing the tagged protein/antibody complexes, and mixed with gentle rotation for 1 to 2 hours at room temperature. The antibodies within the serum, including those that specifically bind the tagged protein, are bound by the protein A/G beads. The protein A/G Sepharose beads are then washed in a suitable buffer (typically 10 mM Tris-HCl pH 7.4, 100 mM NaCl/1 mM EDTA/1% Triton X-100) to remove any unbound tagged protein. This may be achieved by three rounds of centrifugation, removal of the supernatant, and resuspension in buffer. The beads, some with tagged protein attached, are then collected and placed in a fluorescence reader, for example a Spectra Max Gemini XS plate reader from Molecular Devices Inc. The presence of specific autoantibodies/antibodies in the original serum sample is quantitated. In the case of GFP this uses excitation at wavelength 472 nm and emission at 512 nm. The fluorescence excitation will depend upon the fluorophore/tag that is used but it would be possible to combine several different tagged proteins in the same time. For example, different mutant PLY polypeptides and/or fragments thereof may be separately tagged and separately or simultaneously assayed. The sensitivity of the method is dependent on the detection device and can be considerably enhanced by using more sensitive detection devices. Various modifications of these methods could also be utilized.

The assays described herein for detecting antibodies immunoreactive with streptococcal antigens may also be combined with other assays useful for detecting streptococcal infection. For instance, these assays (i.e., ELISA) may be combined with polymerase chain reaction (PCR) assays for detecting streptococcal nucleic acid in a biological sample. Alternatively, an ELISA assay may be combined with an immunoprecipitation assay. Or, a PCR-based assay may be combined with an immunoprecipitation assay. Combining the various assays described herein may serve to even further increase the sensitivity of detection and further decrease the negative predictive value of the data.

As previously mentioned, expression vectors may also be suitable for use. Expression vectors are typically comprised of a flanking sequence operably linked to a heterologous nucleic acid sequence encoding a polypeptide (the "coding sequence"). In other embodiments, or in combination with such embodiments, a flanking sequence is preferably capable of effecting the replication, transcription and/or translation of the coding sequence and is operably linked to a coding sequence. To be "operably linked" indicates that the nucleic acid sequences are configured so as to perform their usual function. For example, a promoter is operably linked to a coding sequence when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered operably linked to the coding sequence. Flanking sequences may be homologous (i.e., from the same species and/or strain as the host cell), heterologous (i.e., from a species other than the host cell species or strain), hybrid (i.e., a combination of flanking sequences from more than one source), or synthetic. A flanking sequence may also be a sequence that normally functions to regulate expression of the nucleotide sequence encoding the polypeptide in the genome of the host may also be utilized.

In certain embodiments, it is preferred that the flanking sequence is a transcriptional regulatory region that drives high-level gene expression in the target cell. The transcriptional regulatory region may comprise, for example, a promoter, enhancer, silencer, repressor element, or combinations thereof. The transcriptional regulatory region may be either constitutive or tissue- or cell-type specific (i.e., the region drives higher levels of transcription in one type of tissue or cell as compared to another). As such, the source of a transcriptional regulatory region may be any prokaryotic or eukaryotic organism, any vertebrate or invertebrate organism, or any plant, provided that the flanking sequence is functional in, and can be activated by, the host cell machinery. A wide variety of transcriptional regulatory regions may be utilized.

Suitable transcriptional regulatory regions include, among others, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); and the major early and late adenovirus gene promoters; the SV40 early promoter region (Bernoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Tissue- and/or cell-type specific transcriptional control regions include, for example, the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region in testicular, breast, lymphoid and mast cells (Leder et al., 1986, *Cell* 45:485-95); the albumin gene control region in liver (Pinkert et al., 1987, *Genes and Devel.* 1:268-

76); the alpha-feto-protein gene control region in liver (Krumlauf et al., 1985, *Mol. Cell. Biol.* 5:1639-48; Hammer et al., 1987, *Science* 235:53-58); the alpha 1-antitrypsin gene control region in liver (Kelsey et al., 1987, *Genes and bevel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., 1987, *Cell* 48:703-12); the myosin light chain-2 gene control region in skeletal muscle (Sani, 1985, *Nature* 314:283-86); and the gonadotropic releasing hormone gene control region in the hypothalamus (Mason et al., 1986, *Science* 234:1372-78), and the tyrosinase promoter in melanoma cells (Hart, I. Semin Oncol 1996 February; 23(1):154-8; Siders, et al. Cancer Gene Ther 1998 September-October; 5(5):281-91). Other suitable promoters are known in the art.

The nucleic acid molecule may be administered as part of a viral and non-viral vector. In one embodiment, a DNA vector is utilized to deliver nucleic acids encoding the targeted immunogen and/or associated molecules (i.e., co-stimulatory molecules, cytokines or chemokines) to the patient. In doing so, various strategies may be utilized to improve the efficiency of such mechanisms including, for example, the use of self-replicating viral replicons (Caley, et al. 1999. *Vaccine*, 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.*, 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of nucleic acids encoding co-stimulatory molecules, cytokines and/or chemokines (Xiang, et al. 1995. *Immunity*, 2: 129-135; Kim, et al. 1998. *Eur. J. Immunol.*, 28: 1089-1103; Iwasaki, et al. 1997. *J. Immunol.* 158: 4591-3601; Sheerlinck, et al. 2001. *Vaccine*, 19: 2647-2656), incorporation of stimulatory motifs such as CpG (Gurunathan, supra; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature*, 408: 605-609; Hanke, et al. 1998. *Vaccine*, 16: 439-445; Amara, et al. 2001. *Science*, 292: 69-74), proteasome-sensitive cleavage sites, and the use of mucosal delivery vectors such as *Salmonella* (Darji, et al. 1997. *Cell*, 91: 765-775; Woo, et al. 2001. *Vaccine*, 19: 2945-2954). Other methods are known in the art, some of which are described below.

Various viral vectors that have been successfully utilized for introducing a nucleic acid to a host include retrovirus, adenovirus, adeno-associated virus (AAV), herpes virus, and poxvirus, among others. The vectors may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NM 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.*, 5 (3): 343-79; Culver, K., et al., *Cold Spring Harb. Symp. Quant. Biol.*, 59: 685-90); Oldfield, E., 1993, *Hum. Gene Ther.*, 4 (1): 39-69). The producer cell line is engineered to produce a viral vector and releases viral particles in the vicinity of the target cell. A portion of the released viral particles contact the target cells and infect those cells, thus delivering a nucleic acid to the target cell. Following infection of the target cell, expression of the nucleic acid of the vector occurs.

Adenoviral vectors have proven especially useful for gene transfer into eukaryotic cells (Rosenfeld, M., et al., 1991, *Science*, 252 (5004): 431-3; Crystal, R., et al., 1994, *Nat. Genet.*, 8 (1): 42-51), the study of eukaryotic gene expression (Levrero, M., et al., 1991, *Gene*, 101 (2): 195-202), vaccine development (Graham, F. and Prevec, L., 1992, *Biotechnology*, 20: 363-90), and in animal models (Stratford-Perricaudet, L., et al., 1992, *Bone Marrow Transplant.*, 9 (Suppl. 1): 151-2; Rich, D., et al., 1993, *Hum. Gene Ther.*, 4 (4): 461-76). Experimental routes for administering recombinant Ad to different tissues in vivo have included intratracheal instillation (Rosenfeld, M., et al., 1992, *Cell*, 68 (1): 143-55) injection into muscle (Quantin, B., et al., 1992, *Proc. Natl. Acad. Sci. U.S.A.*, 89 (7): 2581-3), peripheral intravenous injection (Herz, J., and Gerard, R., 1993, *Proc. Natl. Acad. Sci. U.S.A.*, 90 (7): 2812-6) and stereotactic inoculation to brain (Le Gal La Salle, G., et al., 1993, *Science*, 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.*, 81 (20): 6466-70). And Herpes Simplex Virus type-1 (HSV-1) is yet another attractive vector system, especially for use in the nervous system because of its neurotropic property (Geller, A., et al., 1991, *Trends Neurosci.*, 14 (10): 428-32; Glorioso, et al., 1995, *Mol. Biotechnol.*, 4 (1): 87-99; Glorioso, et al., 1995, *Annu. Rev. Microbiol.*, 49: 675-710).

Poxvirus is another useful expression vector (Smith, et al. 1983, *Gene*, 25 (1): 21-8; Moss, et al, 1992, *Biotechnology*, 20: 345-62; Moss, et al, 1992, *Curr. Top. Microbiol. Immunol.*, 158: 25-38; Moss, et al. 1991. *Science*, 252: 1662-1667). Poxviruses shown to be useful include vaccinia, NYVAC, avipox, fowlpox, canarypox, ALVAC, and ALVAC(2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494,807). The deletion loci were also engineered as recipient loci for the insertion of foreign genes. The deleted regions are: thymidine kinase gene (TK; J2R) vP410; hemorrhagic region (u; B13R+B14R) vP553; A type inclusion body region (ATI; A26L) vP618; hemagglutinin gene (HA; A56R) vP723; host range gene region (C7L-K1L) vP804; and, large subunit, ribonucleotide reductase (I4L) vP866. NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265,189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use (see, for example, U.S. Pat. No. 5,756,103). ALVAC(2) is identical to ALVAC(1) except that ALVAC(2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC(1) and ALVAC (2) have been demonstrated to be useful in expressing foreign DNA sequences, such as TAs (Tartaglia et al., 1993 a,b; U.S. Pat. No. 5,833,975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in certain embodiments. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.). Bacterial vectors may also be used. These vectors include, for example, Shigella, Salmonella, Vibrio cholerae, Lactobacillus, Bacille calmette guérin (BCG), and Streptococcus (see for example, WO 88/6626; WO 90/0594; WO 91/13157; WO 92/1796; and WO 92/21376). Many other non-viral plasmid expression vectors and systems are known in the art and may be used.

Other delivery techniques may also suffice including, for example, DNA-ligand complexes, adenovirus-ligand-DNA complexes, direct injection of DNA, $CaPO_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, Trends Biochem. Sci., 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

A cultured cell comprising the vector is also provided. The cultured cell may be a cultured cell transfected with the vector or a progeny of the cell, wherein the cell expresses the immunogenic polypeptide. Suitable cell lines are known to those of skill in the art and are commercially available, for example, through the American Type Culture Collection (ATCC). The transfected cells can be used in a method of producing an immunogenic polypeptide. The method comprises culturing a cell comprising the vector under conditions that allow expression of the immunogenic polypeptide, optionally under the control of an expression sequence. The immunogenic polypeptide can be isolated from the cell or the culture medium using standard protein purification methods.

The polypeptides and nucleic acids described herein may be combined with one or more pharmaceutically acceptable carriers prior to administration to a host. A pharmaceutically acceptable carrier is a material that is not biologically or otherwise undesirable, i.e., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable pharmaceutical carriers and their formulations are described in, for example, Remingtons: The Science and Practice of Pharmacy, $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of polypeptides and/or fragments thereof to humans or other subjects.

Pharmaceutical compositions may also include carriers, thickeners, diluents, buffers, preservatives, surface active agents, adjuvants, immunostimulants, in addition to the immunogenic polypeptide. Pharmaceutical compositions may also include one or more active ingredients such as antimicrobial agents, antiinflammatory agents and anesthetics. Adjuvants may also be included to stimulate or enhance the immune response. Non-limiting examples of suitable classes of adjuvants include those of the gel-type (i.e., aluminum hydroxide/phosphate ("alum adjuvants"), calcium phosphate, microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPL) of, for example, *E. coli, Salmonella minnesota, Salmonella typhimurium,* or *Shigella exseri*), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAF), saponins (QS-21)), synthetic (muramyl peptide derivatives (murabutide, threony-MDP), nonionic block copolymers (L121), polyphosphazene (PCCP), synthetic polynucleotides (poly A:U, poly I:C), thalidomide derivatives (CC-4407/ACTIMID)), RH3-ligand, or polylactide glycolide (PLGA) microspheres, among others. Fragments, homologs, derivatives, and fusions to any of these toxins are also suitable, provided that they retain adjuvant activity. Suitable mutants or variants of adjuvants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that may used include, for example, Ser-63-Lys, Ala-69-Gly,Glu-110-Asp, and Glu-112-Asp mutants.

Metallic salt adjuvants such as alum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL).

In one embodiment of adjuvanted immunization, for example, mPLY polypeptides and/or fragments thereof may be covalently coupled to bacterial polysaccharides to form polysaccharide conjugates. Such conjugates may be useful, for example, as immunogens for eliciting a T cell dependent immunogenic response directed against the bacterial polysaccharide conjugated to the mPLY and/or fragments thereof.

One or more cytokines may also be suitable co-stimulatory components for use with the mPLY polypeptides and/or fragments thereof, either as polypeptides or as encoded by nucleic acids (Parmiani, et al. Immunol Lett 2000 Sep. 15; 74(1): 41-3; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August; 2(4):243-9; Rao, et al. *J. Immunol.* 156: 3357-3365 (1996)), IL-15 (Xin, et al. *Vaccine,* 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood,* 88: 202-210 (1996)), tumor necrosis factor-alpha (TNF-α), or interferon-gamma (INF-γ). Other cytokines may also be suitable for use, as is known in the art.

The term "antibody" or "antibodies" includes whole or fragmented antibodies in unpurified or partially purified form (i.e., hybridoma supernatant, ascites, polyclonal antisera) or in purified form. A "purified" antibody is one that is separated from at least about 50% of the proteins with which it is initially found (i.e., as part of a hybridoma supernatant or ascites preparation). Preferably, a purified antibody is separated from at least about 60%, 75%, 90%, or 95% of the proteins with which it is initially found. Suitable derivatives may include fragments (i.e., Fab, $Fab_2$ or single chain antibodies (Fv for example)), as are known in the art. The antibodies may be of any suitable origin or form including, for example, murine (i.e., produced by murine hybridoma cells), or expressed as humanized antibodies, chimeric antibodies, human antibodies, and the like.

Methods of preparing and utilizing various types of antibodies are well-known to those of skill in the art and would be suitable for use (see, for example, Harlow, et al. *Antibodies: A Laboratory Manual,* Cold Spring Harbor Laboratory, 1988; Harlow, et al. *Using Antibodies: A Laboratory Manual, Portable Protocol No.* 1, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816, 567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (i.e., about −20° C. or −70° C.), in lyophilized form, or under normal refrigeration conditions (i.e., about 4° C.). When stored in liquid form, it is preferred that a suitable buffer such as Tris-buffered saline (TBS) or phosphate buffered saline (PBS) is utilized. Antibodies and their derivatives may be incorporated into compositions described herein for use in vitro or in vivo. Other methods for making and using antibodies available to one of skill in the art may also be suitable for use.

Also provided herein are kits for detecting the presence of *streptococcus* infection in a patient by detecting antibodies or nucleic acid in a biological sample of the patient. In one embodiment, one or more antigens (e.g., mPLY polypeptides and/or fragment thereof) may form part of a kit for detecting or diagnosing anti-streptococcal antibodies in a biological sample. The antigens may be provided in a suitable container such as a vial in which the contents are protected from the external environment. Thus, a kit for detecting an anti-streptococcal antibody in a sample may comprise one or more mutant PLY polypeptides and/or fragments thereof along with one or more detection reagents for determining binding of one or more antibodies in a sample to the antigen is provided. The kit preferably includes: (i) one or more isolated and purified mPLY polypeptides and/or fragments thereof; and, (ii) a system for detecting the formation of an antigen-antibody complex, optionally packaged with instructions for use. The antigen may be free in solution or may be immobilized on a solid support, such as a magnetic bead, tube, microplate well, or chip. In certain embodiments, a solid matrix comprising an isolated and purified mPLY polypeptides and/or fragments thereof or a fusion protein or protein aggregate adsorbed thereto is provided. In some embodiments, the kit may further comprise an antibody-binding molecule as a detection reagent. The antibody-binding molecule may be a capture or detection reagent and may be free in solution or may be immobilized on a solid support, such as a magnetic bead, tube, microplate well, or chip. The antibody-binding molecule or polypeptide may be labeled with a detectable label, for example a fluorescent or chromogenic label or a binding moiety such as biotin. Suitable labels are described in more detail above. The kit may further comprise detection reagents such as a substrate, for example a chromogenic, fluorescent or chemiluminescent substrate, which reacts with the label, or with molecules, such as enzyme conjugates, which bind to the label, to produce a signal, and/or reagents for immunoprecipitation (i.e., protein A or protein G reagents). The detection reagents may further comprise buffer solutions, wash solutions, and other useful reagents. The kit may also comprise one or both of an apparatus for handling and/or storing the sample obtained from the individual and an apparatus for obtaining the sample from the individual (i.e., a needle, lancet, and collection tube or vessel). The kit may also include instructions for use of the antigen, e.g. in a method of detecting anti-streptococcal antibodies in a test sample, as described herein. Where the assay is to be combined with another type of assay such as PCR, the required reagents for such an assay (i.e., primers, buffers and the like) along with, optionally, instructions for the use thereof, may also be included.

It must be noted that, as used in the specification and the appended claims, the singular forms "a", "an", and "the" include plural referents unless the context clearly dictates otherwise. Thus, for example, reference to a fragment may include mixtures of fragments and reference to a pharmaceutical carrier or adjuvant may include mixtures of two or more such carriers or adjuvants.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

When the terms prevent, preventing, and prevention are used herein in connection with a given treatment for a given condition (e.g., preventing infection by *Streptococcus* sp.), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patients experiencing fewer and/or milder symptoms of the condition than otherwise expected. A treatment can "prevent" infection by resulting in the patients displaying only mild overt symptoms of the infection; it does not imply that there must have been no penetration of any cell by the infecting microorganism.

Similarly, reduce, reducing, and reduction as used herein in connection with the risk of infection with a given treatment (e.g., reducing the risk of a pneumococcal infection) typically refers to a subject developing an infection more slowly or to a lesser degree as compared to a control or basal level of developing an infection in the absence of a treatment (e.g., administration or vaccination using mPLY). A reduction in the risk of infection may result in the patients displaying only mild overt symptoms of the infection or delayed symptoms of infection; it does not imply that there must have been no penetration of any cell by the infecting microorganism.

All references cited within this disclosure are hereby incorporated by reference in their entirety. Certain embodiments are further described in the following examples. These embodiments are provided as examples only and are not intended to limit the scope of the claims in any way.

EXAMPLES

Example 1

Generation of Expression Plasmids for wtPLY and his-Tagged wtPLY

The ply gene encoding wtPLY was cloned by PCR using primers Spn001 (CATGCCATGGCAAATAAAGCAG-TAAATGAC; SEQ ID NO. 45) and Spn002 (CAGCCGCTC-GAGCTAGTCATTTTCTACCTTATCCTC; SEQ ID NO. 46) from *S. pneumoniae* strain R36A (SEQ ID NO. 1, GenBank Accession No. M17717). The PCR product was digested with restriction enzymes NcoI and XhoI and cloned into plasmid pTrcK. Plasmid pTrcK is a kanamycin-resistant derivative of plasmid pTrcHis2 (Invitrogen). The plasmid thus generated (pBM46) was used for expression of wtPLY (producing a non-tagged PLY polypeptide) under control of the trc promoter. The DNA sequence of the amplicon was identical to the published ply sequence shown in SEQ ID NO. 1), encoding the deduced amino acid sequence shown in SEQ ID NO. 2. The wtPLY-encoding nucleic acid was then transferred into pET-28a (EMD Biosciences Cat. No. 69864-3) (NcoI-XhoI), resulting in plasmid pJMS102 (providing non-tagged wtPLY expression from the T7 promoter). The same gene was then cloned by PCR using primers 14913.JY (GAAGGAGATATCATATGGCAAATAAAGCAG; SEQ ID NO. 47) and 14914.JY (CCTTTCGGGCTTTGTTAG- CAGC; SEQ ID NO. 48) from plasmid pJMS102 back into pET-28a (NdeI-XhoI), resulting in plasmid pJMS112 (providing His-tagged wtPLY expression from the T7 promoter).

Example 2

Generation of Expression Plasmids for PLY (T65C, G293C, C428A) (PlyD1) and His-Tagged PlyD1

Plasmid pJMS112 from Example 1 was used as the template for site-directed mutagenesis to modify the expressed PLY polypeptide. Site-directed mutagenesis was performed using the QuickChange Multi Site-Directed Mutagenesis kit as per the manufacturer's instructions (Agilent Technologies, Stratagene Products Division, La Jolla, Calif.). The following modifications were introduced into the PLY encoding nucleotide sequence:

the codon for Thr65 was changed from ACC to TGC, encoding cysteine (C) in place of threonine (T) (T65C);

the codon for Gly293 was changed from GGG to TGC, encoding cysteine (C) in place of glycine (G) (G293C); and, the codon for Cys428 was changed from a TGT to GCT, encoding alanine (A) in place of cysteine (C) (C428A).

The plasmid resulting from the site-directed mutagenesis was designated pJAY7, and provided for expression of His-tagged PLY(T65C, G293C, C428A) (His-PlyD1). Plasmid pJAY7 was digested with NdeI and XhoI to isolate the 1420 bp ply gene therefrom. This 1420 bp fragment was gel purified and then ligated into NdeI-XhoI cut and dephosphorylated pET-30a (EMD Biosciences Cat. No. 69909-3). The resulting plasmid was named pJMS140, and provided non-tagged PlyD1 expression from the T7 promoter. The sequence of the mutated ply gene encoding PlyD1 was confirmed using the primers shown in Table 3 below.

TABLE 3

| Primer Name | Sequence 5' → 3' | SEQ ID NO. |
|---|---|---|
| T7 Promoter | TAATACGACTCACTATAGGG | 49 |
| 7294.BB | GCTAGTTATTGCTCAGCGG | 50 |
| 13002.MP | CTGCTTTTGAAGCTTTGATA | 51 |
| 13003.MP | AGGCTTGGGACAGAAATGGG | 52 |
| 13005.MP | TTGAAAGGTCGCAACTACAT | 53 |
| 13006.MP | AAACACATCTCCTGGATTTT | 54 |
| 13007.MP | ACTACGAGAAGTGCTCCAGG | 55 |

Sequencing of the mutated ply sequence using the primers of Table 3 confirmed the mutated sequences were as expected. Expression of PlyD1 was confirmed by chemical transformation of E. coli BL21(DE3) with plasmid pJMS140. PlyD1 with a molecular weight of approximately 55 kDa was expressed.

Example 3

Purification of PlyD1 PLY (T65C, G293C, C428A)

To obtain larger quantities of the PlyD1 (SEQ ID NO. 44; T65C, G293C, C428A) was expressed as a recombinant protein (~55 kDa) in pET30A plasmid using an E. coli expression system. The E. coli expressed recombinant PlyD1 protein was grown in a 20-L fermentor. The cells were homogenized at high pressure to release the soluble PlyD1 and diafiltered in Tris buffered saline to produce a crude extract of PlyD1. The crude PlyD1 extract was 0.2 um filtered prior to use. The filtered, crude extract was run through the strong anion exchange Giga Cap Q-650 M column (Tosoh Biosciences). Unbound contaminant proteins were removed in the flow-through and chased with equilibration buffer (20 mM Tris-HCl, pH 8.5). An intermediate wash step was performed using equilibration buffer containing 100 mM NaCl. Bound PlyD1 was eluted with 20 mM Tris-HCl, pH 8.5 containing 250 mM NaCl. PlyD1 material recovered from this column chromatography step was then conditioned with 5M NaCl solution to bring the conductivity up to ~80 mS/cm.

The conditioned PlyD1 material was then subjected to a hydrophobic column chromatography using Phenyl Sepharose FF (GE Health Care). PlyD1 was purified using binding and elution mode. Unbound proteins were removed by washing the column with 1M NaCl equilibration buffer and bound PlyD1 eluted with the 20 mM Tris-HCl buffer, pH 8.0

The phenyl sepharose-purified PlyD1 material was then diluted 4-fold with 5 mM sodium phosphate (pH 6.2) to decrease the conductivity and pH of the binding solution. This material was then further purified using Ceramic Hydroxyapatite type I 40 um resin (BioRad). The equilibration buffer is 5 mM Sodium Phosphate, pH 6.2. PlyD1 was purified a second time using a binding and elution mode on this mixed mode column chromatography resin. Contaminants were removed using 5 mM sodium phosphate, pH 7.0, 750 mM NaCl and bound PlyD1 eluted with 10 mM sodium phosphate, pH 7.0, containing 1 M NaCl.

Figure 4:
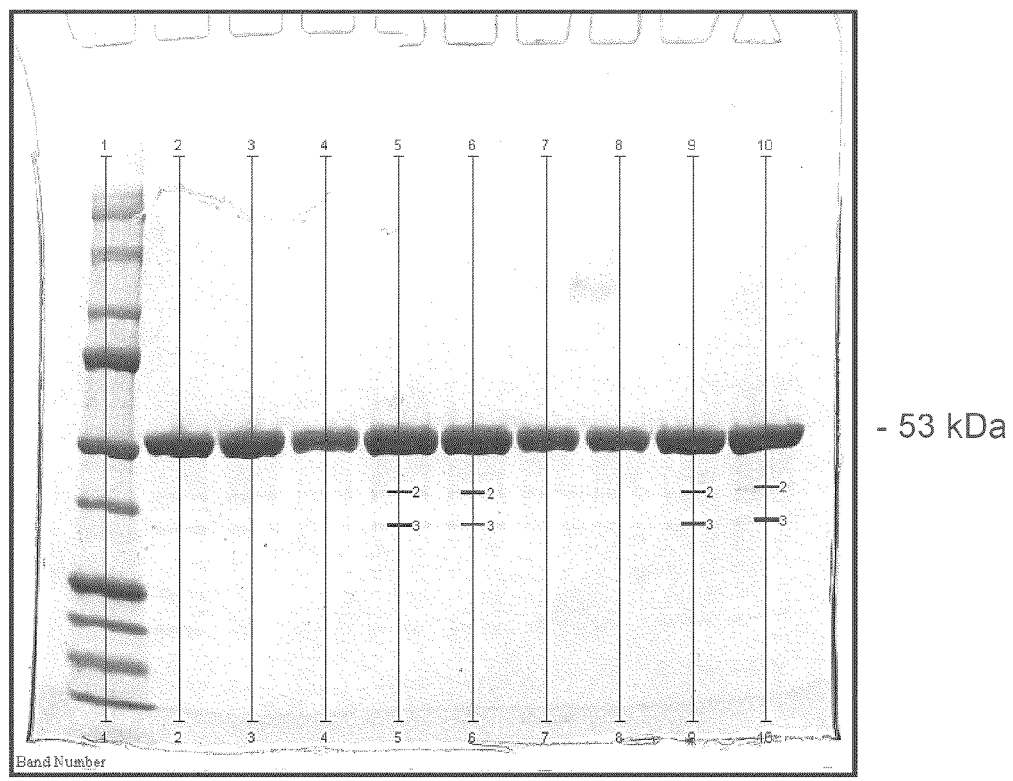
FIG. 4. PlyD1 protein purification based on SDS-PAGE analysis.

After the three column steps, purified PlyD1 was diafiltered in 10 mM Tris-HCl, pH 7.4, 150 mM NaCl buffer. Tween-80 was added to a final concentration of 0.05% to prevent PlyD1 precipitation. The purified PlyDI bulk material was 0.2 μM filtered and subsequently formulated at different concentrations. A typical purification process yields 600-850 mg/L of purified PlyD1 protein with a purity of >98% based on SDS-PAGE analysis (FIG. 4).

Example 4

In Vitro Hemolytic Assay

Cytolytic activity of PLY polypeptides is customarily evaluated by an in vitro hemolysis assay. Generally, test proteins are serially diluted across a plastic microtiter plate in 2-fold serial dilutions with a highest concentration of 0.5 mg/mL of test protein. BSA is included to prevent adsorptive losses on the plastic microtiter plate. Sheep red blood cells are added to all wells, and the plastic microtiter plates are incubated for 30 min. Lysed cells release hemoglobin. For a positive control, 100% lysis measurement is obtained by the addition of 1% Trition X-100. For a negative control, the sheep red blood cells are incubated with PBS alone. The microtiter plate is centrifuged to separate the intact cells from the lysed cells. The supernatant containing the lysed cells are transferred to a fresh plate and subject to an $A_{540}$ hemoglobin release assay. The specific activity is determined as the inverse of protein concentration (mg/mL) at which 50% hemolysis has occurred relative to the positive control. A representative hemolytic assay system is shown below:

1. Add 50 μL Hank's buffered saline solution (HBSS)+ 0.5% (w/v) bovine serum albumin (BSA) to all the wells of a 96 well round-bottomed microtiter plates.
2. Dilute stock of test protein (e.g., PlyD1) and a negative irrelevant protein control to a final concentration of 1 mg/mL with HBSS+0.5% BSA.
3. Prepare a 3% sheep red blood cell (RBC) suspension from 10% stock of washed pooled cells (Rockland Immunochemical, Catalog number R405-0050) by dilution with HBSS+0.5% BSA.

4. Add 50 µL of 1 mg/mL test protein (e.g., PlyD1) (and buffer and irrelevant protein control) to plate 1 column 2, and serially dilute (1:2) across two rows (columns 2-12 in 2 rows). The range of protein concentrations covered will therefore be from 500 µg/mL to 0.000238 µg/mL. Column 1 is reserved for buffer blanks (see step 7 below), negative controls (see step 6 below), and 100% lysis control (see step 5 below).
5. Setup of 100% lysis controls: Remove 10 µL of HBSS+ 0.5% BSA from column 1/rows A-C. Add 10 µL of 10% Triton X-100 in HBSS+0.5% BSA and 50 µL of 3% sheep RBC solution (from #3 above) to each of those wells.
6. Setup of negative controls: Add 50 µL of either 1 or 3% sheep RBC solution (from step 3 above) to column 1/rows D-F.
7. Setup of buffer blanks: Add 50 µL HBSS+0.5% BSA to column 1/rows G-H.
8. Initiation of reaction: Add 50 µL of 3% sheep RBC solution (from step 3 above) to all of the test wells.
9. Incubate for 30 min at 37° C. with rotary shaking.
10. Add 50 µL of HESS to all wells and centrifuge for 5 min at 1050 g to spin down non-lysed RBC. (Additional saline facilitates subsequent step of withdrawing supernatant without disturbing pellet.)
11. Transfer 80 µL of supernatants to a flat-bottomed microtiter plate, and read absorbances at 540 nm. Plates are blanked with the buffer blanks from step 7. Percent hemolysis is calculated by dividing the absorbance in each test well by the average absorbance of the 100% lysis controls from step 5.
12. The data are plotted as percent hemolysis versus protein concentration (log scale). To determine the specific activity in hemolytic units per milligram of protein (HU/mg): i) determine the protein concentration at the 50% hemolysis point, ii) convert the protein concentration to mg/mL, and iii) take the inverse of the protein concentration.

This system was used to compare the haemolytic activity of the wild-type and mutated PLY polypeptides. Table 4 provides a comparison of the in vitro hemoltyic activity (toxin mediated lysis of sheep red blood cells) of wtPLY and PlyD1 (<0.001%). As shown therein, the mutated PlyD1 polypeptide exhibits significantly decreased haemolytic activity as compared to the wild-type PLY polypeptide.

Example 5

Generation of Anti-PlyD1 Antibodies and Assessment of Antibody-Mediated Inhibition of wtPLY Activity PlyD1 was expressed in *E. coli* and purified as described above. The purified proteins were dialyzed against PBS and used for the immunization of rabbits. Two rabbits were immunized intra-muscularly at 20 µg dose with Freund's adjuvant. The animals received two additional immunizations with incomplete Freund's adjuvant two and four weeks after the initial injection. Serum was collected two and four weeks after the last injection. The generation of antibodies in the rabbit was first tested by western blot to ensure that anti-PlyD1 antibodies react with wtPLY. Rabbit sera may also be tested by ELISA and/or IGEN competition assay using standard procedures to detect the presence of antibodies specific for known neutralizing epitopes. Rabbits immunized with PlyD1 produced IgG antibodies that bind to full length PLY in ELISA and IGEN assays with good serum titres. Thus, production of antibodies reacting with wtPLY following immunization with PlyD1 was determined.

Generally, the assay to determine the ability of anti-PlyD1 antibodies to inhibit wtPLY hemolytic activity involves the following steps. First, antisera are produced essentially as described herein then serially diluted two-fold across a microtiter plate. A constant amount of native wtPLY is added to all wells. Sheep red blood cells are added to all wells and the assay proceeds as per the in vitro hemolysis assay described above. After final plate processing, the data are graphed to determine the 50% inhibition titer. A representative haemolysis-inhibition assay system is shown below:

1. Pre-treat antisera to deplete cholesterol (which is inhibitory to PLY-mediated hemolysis) as follows:
   a. prepare stock solutions of 20 mg/mL solution of dextran sulfate (Dextralip 50) and 1 M $MgCl_2$
   b. prepare the working solution by mixing equal volumes of both stock solutions listed in (a) above
   c. add working solution from (b) above to sera in a 1:10 ratio (i.e. 200 μL working solution to 2 mL sera) and mix thoroughly for 10 sec
   d. incubate at room temperature for 15 min, then centrifuge at 1500×g for 30 min and transfer supernatant to a fresh tube (cholesterol is found in the precipitate)
2. Add 50 μL Hank's buffered saline solution (HESS)+ 0.5% (w/v) bovine serum albumin (BSA) to all the wells of a 96 well round-bottomed microtiter plates.
3. Add 50 μL of each serum to be tested to a separate row in column 2, and serially dilute (1:2) across the entire row. Column 1 is reserved for buffer blanks, and positive and negative controls.
4. Prepare a dilution of purified wild-type PLY (non-tagged, lot DC5826) such that 25 uL contains 10 ng of protein (using HBSS+0.5% BSA).
5. Add 25 uL (containing 10 ng) of diluted wild-type PLY to all wells except column 1 and allow to incubate with diluted antisera for 30 min at 37 degrees C. with shaking at 250 rpm.
6. Prepare a 3% sheep red blood cell (RBC) suspension from 10% stock of washed pooled cells (Rockland Immunochemical, Catalog number R405-0050) by dilution with HBSS+0.5% BSA.
7. Setup of 100% lysis controls: Add 15 μL of HBSS+0.5% BSA and 10 μL of 10% Triton X-100 in HBSS+0.5% BSA to column 1/rows A and B. Add and 25 μL of 1 or 3% sheep RBC solution (from #6 above) to each of those wells.
8. Setup of positive controls: Add 25 μL of diluted wild-type Ply (from #4 above) to column 1/rows C and D. Add and 25 μL of 3% sheep RBC solution (from #6 above) to each of those wells.
9. Setup of negative controls: Add 25 μL HBSS+0.5% BSA and 25 μL of 3% sheep RBC solution (from #6 above) to column 1/rows E and F.
10. Setup of buffer blanks: Add 50 μL HBSS+0.5% BSA to column 1/rows G and H.
11. Initiation of reaction: Add 25 μL of 3% sheep RBC solution (from #6 above) to all of the test wells.
12. Incubate for 30 min at 37° C. with shaking at 250 rpm.
13. Centrifuge for 5 min at 1050 g to remove non-lysed RBC.
14. Transfer 75 μL of supernatants to a flat-bottomed microtiter plate, and read absorbances at 540 nm. Plates are blanked with the buffer blanks from step 10. Percent hemolysis is calculated by dividing the absorbance in each test well by the average absorbance of the 100% lysis controls from step 7.

This system was used to test the antibodies produced following immunization with PlyD1. The data are plotted as percent hemolysis versus antiserum titer (log scale) and the 50% hemolysis inhibition titer is taken as the inverse of the serum dilution at which the percent hemolysis is reduced to 50%. As shown in Table 4 therein, the 50% hemolysis inhibition titer of PlyD1 and the mPLYs modified at G293 (to threonine, valine or cysteine) is similar to wtPLY. A summary of the characteristics observed for PlyD1 polypeptide is provided in Table 4.

TABLE 4

|  | 50% hemolysis inhibition titer | | Hemolytic activity |
| --- | --- | --- | --- |
|  | Test 1 | Test 2 | (% vs. wtPLY) |
| prebleed | 4 | 4 | NA |
| Anti-wtPLY | 256-512 | 2048 | 100% |
| Anti-PdB | 256-512 | ND | 1%* |
| Anti-PlyD1 (T65C, G293C, C428A) | 256-512 | ND | <0.001% |
| Anti-Ply (G293T/V/C) | ND | 4096 | <0.001% |

*Observed value for his-tagged PdB was about 0.5%; observed values for his-tagged wtPLY, and PlyD1 were about equivalent to the corresponding untagged polypeptides.

FIG. 2 shows that other PLY mutants, including Ply-G293A (G293 substituted by alanine), Ply-G293T (G293 substituted by threonine), Ply-G293V (G293 substituted by valine), and Ply-G293C (G293 substituted by cysteine) also showed lower hemolytic activity (including no detectable activity) than wtPLY ("Ply" in FIG. 4). Additional independent lots of PlyD1 were also tested. Hemolytic activity was not detected in any of the PlyD1 lots.

Example 6

Immunogenicity of PlyD1 and Adjuvantation

To investigate the immunogenicity of varying doses of PlyD1, either alone or in presence of AlOOH adjuvant or stored at different temperature to evaluate its stability. Two studies were performed in mice using PlyD1 as an immunogen. In a first study, PlyD1 was administered in varying doses, with or without aluminum hydroxide (A100H) adjuvant. PlyD1 was found to induce high anti-PLY IgG titers and hemolysis inhibition (HI) titers at all doses tested.

In a second study, PlyD1 was administered with AlOOH adjuvant following two-weeks storage at −70° C., 2-8° C., or 45° C. PlyD1 was administered in varying doses, with or without AlOOH adjuvant. Mice were immunized three times, three weeks apart, and blood samples were taken three weeks after each immunization. Antibody titers from the second and final bleeds (three weeks following last immunization) were measured using PLY-specific ELISA. ELISA titers showed a dose response for anti-PLY titers following the second and third bleed. Immunization with adjuvanted PlyD1 resulted in significantly higher anti-PLY titers compared to those induced by unadjuvanted PlyD1. ELISA results from the third bleed are shown in Table 5.

TABLE 5

PLY-specific Antibody Titers for Groups of Mice Immunized with Placebo or Increasing Amount of PlyD1, with or without AlOOH

| Group | Bleed* | ELISA Mean Titer |
| --- | --- | --- |
| PlyD1-adjuvanted (1 μg) | Pre-immunization | <100 |
|  | Post 3$^{rd}$ immunization | 16890 |
| PlyD1-adjuvanted (2.5 μg) | Pre-immunization | <100 |
|  | Post 3$^{rd}$ immunization | 20319 |
| PlyD1-adjuvanted (5 μg) | Pre-immunization | <100 |
|  | Post 3$^{rd}$ immunization | 44572 |
| PlyD1-adjuvanted (10 μg) | Pre-immunization | <100 |
|  | Post 3$^{rd}$ immunization | 41587 |
| PlyD1 (1 μg) | Pre-immunization | <100 |
|  | Post 3$^{rd}$ immunization | 2934 |
| PlyD1 (2.5 μg) | Pre-immunization | <100 |
|  | Post 3$^{rd}$ immunization | 1393 |
| PlyD1 (5 μg) | Pre-immunization | <100 |
|  | Post 3$^{rd}$ immunization | 6859 |
| PlyD1 (2.5 μg) | Pre-immunization | <100 |
|  | Post 3$^{rd}$ immunization | 5572 |

In this second study, the ability of antisera from PlyD1-immunized mice to inhibit PLY-mediated hemolysis of sheep red blood cells was tested using the HI assay following the third bleed was also assessed. While the HI titers appeared to be slightly higher in mice immunized with adjuvanted PlyD1 versus unadjuvanted PlyD1, this difference is considered to be within the assay variation and is therefore not significant. Furthermore, there did not appear to be a dose response in the HI titers generated with increasing amounts of PlyD1. Results are shown in Table 6.

TABLE 6

Hemolysis Inhibition Titers in Sera of Mice Immunized with PlyD1 with or without AlOOH

| Immunization | Prebleed HI Titer* | Bleed III HI Titer | Fold Increase in HI Titer |
| --- | --- | --- | --- |
| PlyD1-adjuvanted (1 μg) | 2 | 64 | 32 |
| PlyD1-adjuvanted (2.5 μg) | 2 | 64 | 32 |
| PlyD1-adjuvanted (5 μg) | 2 | 64 | 32 |
| PlyD1-adjuvanted (10 μg) | 2 | 64 | 32 |
| PlyD1 (1 μg) | 2 | 16 | 8 |
| PlyD1 (2.5 μg) | 2 | 32 | 16 |
| PlyD1 (5 μg) | 2 | 32 | 16 |
| PlyD1 (10 μg) | 2 | 32 | 16 |

*HI Titer: highest serum dilution able to completely inhibit hemolysis of a given quantity of recombinant wild-type PLY. The lower limit of detection of the assay is 4; titers lower than 4 are listed as 2 for statistical purposes.

As shown herein, PlyD1 generated high anti-PLY IgG titers when PlyD1, stored at either −70° C. or 2-8° C. was used for immunization, but not PlyD1 stored at 45° C. Moreover, in the presence of adjuvant, PlyD1 was able to generate higher titers of anti-PLY-specific antibodies in comparison to PlyD1 administered without adjuvant.

These studies show that immunization with PlyD1 elicited neutralizing antibodies at all PlyD1 doses tested. Furthermore, the data indicate that the immune response to PlyD1 benefits from an adjuvant by generating quantitatively more neutralizing antibodies against PLY.

Example 7

TLR4 Assay wtPLY is known to activate macrophages to generate cytokines (Malley, et al. PNAS USA, 100(4):1966-71 (2003)). This assay determines macrophage activation by PlyD1 by measuring PlyD1-induced cytokine production in vitro. J774 (mouse) and MM6 (human) macrophage-like cells were incubated overnight with PdB, PlyD1 or PLY treated (+/+) or not treated (−/−) with proteinase K and heat. Heat was used in order to distinguish any false positive results due to lipopolysaccharide (LPS) contamination in the treated group. Cytokine production (IL-6, IL-10, TNF-α, IL-1β) was measured by ELISA after overnight incubation. No induction of cytokines (IL-1β, IL-6 and IL-10) was detected following co-culture of mouse or human macrophage cell lines (J774A.1 or MM6, respectively) with PlyD1 either untreated or treated with proteinase K/heat. In comparison, untreated wtPLY was able to induce low amounts of IL-1β and IL-6 cytokine release in MM6 cells (PLY −/−).

Example 8

Immunogenicity of PlyD1 In Vivo

In testing the immunogenicity of PlyD1 in the models described below, IgG responses elicited by PlyD1 or PdB were tested by ELISA using recombinant wtPLY as the coating antigen. A standard assay protocol was used.

A. Sepsis Model

The ability of PlyD1 to induce anti-PLY antibodies and induce a protective immune response in mice was assessed. Groups of female BALB/c mice (N=15 per group) were immunized subcutaneously (SC) with purified recombinant PlyD1 or PdB at varying doses, formulated in TB S-containing aluminum adjuvant (260 μg/dose). PdB was administered at 10 μg/dose and PlyD1 at 1 μg, 2.5 μg, 5 μg, and 10 μg/dose. The injection volume was 200 μL per dose. TBS placebo-containing aluminum adjuvant was injected into negative control groups. Animals were immunized SC at 0, three and six weeks following initiation of the study. At nine weeks, animals were challenged by intranasal (IN) injection with $10^7$ colony forming units (cfu) of S. pneumoniae serotype 6B in phosphate-buffered saline (PBS) suspension (50 μL challenge volume per mouse). Following the challenge, mice were monitored for mortality daily. Fourteen days post-challenge, all surviving mice were euthanized. The Fisher Exact Test was used to determine if there was a significant difference between the immunized group(s) and the placebo control. In addition, sample bleeds were taken from all animals following the second boost (day 42) and prior to challenge, following three immunizations (day 63). Sera were analyzed for total pneumolysin-specific IgG response by means of an antibody ELISA and for pneumolysin neutralizing capacity in an inhibition of hemolysis assay.

The differences in time-to-death between mice injected with vaccines and mice injected with placebo were assessed using survival distribution functions with product-limit approach. Although antibodies were induced as shown below, using this sepsis model, mice vaccinated with PlyD1 did not show delays in time-to-death compared with placebo group, based on Wilcoxon test (p=0.5458 for 1 μg, p=0.5003 for 2.5 μg, p=0.1448 for 5 μg, and p=0.1723 for 10 μg). Although there was an apparent dose effect with PlyD1, none of the groups immunized with PlyD1 showed significant survival or delay to death compared to the placebo control group (p>0.05) (Table 7).

TABLE 7

Percent Survival of Mice Immunized with Placebo, PdB or PlyD1 and Challenged with Serotype 6B

| Day | Placebo (PBS) | PdB (10 μg) | PlyD1 (1 μg) | PlyD1 (2.5 μg) | PlyD1 (5 μg) | PlyD1 (10 μg) |
|---|---|---|---|---|---|---|
| 0 | 100 | 100 | 100 | 100 | 100 | 100 |
| 1 | 100 | 100 | 100 | 100 | 100 | 100 |
| 2 | 60 | 100 | 80 | 80 | 93 | 86 |
| 3 | 60 | 100 | 80 | 80 | 93 | 86 |
| 4 | 60 | 93 | 80 | 60 | 93 | 79 |
| 5 | 60 | 93 | 67 | 53 | 73 | 79 |
| 6 | 60 | 80 | 60 | 53 | 60 | 71 |
| 7 | 40 | 67 | 47 | 47 | 60 | 64 |
| 8 | 40 | 67 | 47 | 47 | 60 | 64 |
| 9 | 40 | 67 | 47 | 47 | 60 | 57 |
| 10 | 40 | 67 | 47 | 47 | 60 | 57 |
| 11 | 33 | 67 | 40 | 47 | 60 | 57 |
| 12 | 33 | 67 | 40 | 47 | 60 | 57 |
| 13 | 33 | 67 | 40 | 47 | 60 | 57 |
| 14 | 33 | 67 | 40 | 47 | 60 | 57 |
| p-value[1] survival | | 0.0716 | 0.5000 | 0.3552 | 0.1362 | 0.1804 |
| p-value[2] delay to death | | 0.0411 | 0.5458 | 0.5003 | 0.1448 | 0.1723 |

[1]p value was determined according to the fisher exact test and test groups were compared to placebo control.
[2]p value was determined according to the Wilcoxon test and test groups were compared to placebo control.

Under this sepsis model, ELISA was performed on days 42 and 63 post immunization. Results showed high titers of anti-PLY antibodies at all doses tested. On day 42 and 63, all immunized mice had antibody responses against wtPLY, but a significant increase in antibody titer was not observed after the third vaccination. The anti-PLY IgG titers were not dose dependent. Pneumolysin-specific antibody titers in the PBS placebo-, PdB- and PlyD1-immunized groups are summarized in Table 8 following the third immunization. Functional antibody titers as measured by inhibition of hemolysis were higher at day 63 compared to day 42 in all the groups tested (data not shown).

TABLE 8

PLY-Specific Antibody Titers for Groups of Mice Immunized with Placebo, PdB or PlyD1

| Group | Bleed[1] | ELISA Mean Titer |
|---|---|---|
| PBS Placebo | Pre-immunization | <100 |
| | Pre-challenge | <100 |
| PdB (10 μg) | Pre-immunization | <100 |
| | Pre-challenge | 43702 |
| PlyD1 (1 μg) | Pre-immunization | <100 |
| | Pre-challenge | 87968 |
| PlyD1 (2.5 μg) | Pre-immunization | <100 |
| | Pre-challenge | 69066 |
| PlyD1 (5 μg) | Pre-immunization | <100 |
| | Pre-challenge | 66912 |
| PlyD1 (10 μg) | Pre-immunization | <100 |
| | Pre-challenge | 76837 |

[1]Pre-challenge anti-PLY titers were determined for individual mice and are represented as the geometrical mean.

As shown herein, using this sepsis model, immunization with recombinant PlyD1 protein generated specific IgG responses but did not show significant protection against lethal IN challenge with a *S. pneumoniae* serotype 6B strain. However, sera from mice immunized with PlyD1 demonstrated PLY-neutralizing capacity.

B. Focal Pneumonia Model

PlyD1 was also tested using a focal pneumonia mouse model. Briefly, groups of 10 CBA/N mice were immunized SC with purified recombinant PlyD1 proteins at variable doses formulated in TBS-containing aluminum adjuvant (300 µg/dose). The injection volume was 200 µL per dose. Phosphate-buffered saline placebo-containing aluminum adjuvant was injected into negative control groups. Animals were immunized SC three times at 0, three and six weeks following initiation of the study. Three weeks after the last immunization, animals were challenged intranasally (IN) with $3-7\times10^6$ cfu of *S. pneumoniae* strain EF3030 (serotype 19F; 40 µL challenge volume per mouse). Mice were sacrificed 5 days post-challenge and lung tissue harvested and plated for cfu recovery. The Mann-Whitney Test was used to determine if there was a significant difference between immunized group(s) and the placebo control group. In studies using this model, sera analysis for either IgG titer or neutralizing capacity of the sera was not performed. All groups that were immunized with PlyD1 did not have significantly lower bacterial lung burden when compared to the PBS-immunized group and thus, were considered as not protected (data not shown).

C. Intranasal Challenge Model

PlyD1 was also evaluated in-house using an intranasal challenge mouse model. In this model, groups of female CBA/j mice (N=15 per group) were immunized IM with purified recombinant PlyD1 proteins at doses ranging from 0.25 to 25 µg/dose. PlyD1 was formulated in TBS-containing aluminum adjuvant (65 µg/dose). The injection volume was 50 µL per dose. PBS placebo-containing aluminum adjuvant was injected into negative control groups. Animals were immunized IM at 0, 3, and 6 weeks following initiation of the study. At nine weeks, animals were challenged IN with a lethal dose ($5\times10^5$ cfu) of *S. pneumoniae* strain 14453 (serotype 6B) in PBS suspension (40 µL challenge volume per mouse). Following the challenge, mice were monitored daily for mortality. All surviving mice were euthanized 11 days post-challenge. The Fisher Exact Test was used to determine if there was a significant difference between the immunized group(s) and the placebo control. In addition, sample bleeds were taken from all animals 4 days prior to the first injection (pre-immunization at 0 weeks) and following each immunization. Sera were analyzed for total PlyD1-specific IgG responses by means of an antibody ELISA and for pneumolysin neutralizing capacity in an inhibition of hemolysis assay.

PlyD1 was administered at 0.25 µg, 0.5 µg, 1 µg, 5 µg, 10 µg and 25 µg/dose or an adjuvant alone (placebo). Mice were immunized three times, three weeks apart and blood samples were taken three weeks following each immunization. Antibody titers from the second bleed and final bleed (three weeks following last immunization) were measured using PLY-specific ELISA. The ability of the first, second and final bleed sera to inhibit PLY-mediated hemolysis was assessed. Mice were challenged with *S. pneumoniae* strain 14453 (serotype 6B) at $5\times10^5$ cfu/dose three weeks following the last immunization and survival was monitored for ten days. Survival of mice immunized with PlyD1 was significantly better than placebo group at doses of 5, 2.5 and 0.25 µg/dose, indicating that protection is not dose-dependent. The best protection was observed at 2.5 µg/dose, in which 60% of the mice survived compared to none in the placebo group. The results are summarized in Table 9.

TABLE 9

Percent Survival of Mice Immunized with Placebo or PlyD1 at Various Doses and Challenged with *S. pneumoniae* Strain 14453

| Day | Placebo (AlOOH) | PlyD1 (25 µg) | PlyD1 (10 µg) | PlyD1 (5 µg) | PlyD1 (2.5 µg) | PlyD1 (1 µg) | PlyD1 (0.5 µg) | PlyD1 (0.25 µg) |
|---|---|---|---|---|---|---|---|---|
| 0 | 100 | 100 | 100 | 100 | 100 | 100 | 100 | 100 |
| 1 | 100 | 100 | 100 | 100 | 100 | 100 | 100 | 100 |
| 2 | 100 | 100 | 100 | 100 | 100 | 100 | 100 | 100 |
| 3 | 91.7 | 100 | 91.7 | 100 | 100 | 90.1 | 100 | 100 |
| 4 | 41.7 | 83.3 | 58.3 | 91.7 | 66.7 | 45.5 | 75 | 75 |
| 5 | 8.3 | 50 | 41.7 | 50 | 58.3 | 36.4 | 33.3 | 58.3 |
| 6 | 8.3 | 50 | 33.3 | 50 | 58.3 | 36.4 | 25 | 58.3 |
| 7 | 0 | 16.7 | 16.7 | 41.7 | 58.3 | 18.2 | 16.7 | 58.3 |
| 8 | 0 | 16.7 | 16.7 | 41.7 | 58.3 | 18.2 | 16.7 | 41.7 |
| 9 | 0 | 16.7 | 16.7 | 41.7 | 58.3 | 18.2 | 16.7 | 41.7 |
| 10 | 0 | 16.7 | 16.7 | 41.7 | 58.3 | 18.2 | 16.7 | 41.7 |
| p-value[1] survival | | 0.239 | 0.239 | 0.0466 | 0.0023 | 0.26 | 0.239 | 0.0466 |

[1]p value was determined according to the fisher exact test and test groups were compared to placebo control.

The ability of antisera from mice immunized using this intranasal challenge model was also assessed for inhibition of PLY-mediated hemolysis of sheep red blood cells. Sera from all bleeds were pooled according to their treatment groups and tested using the HI assay following the all bleeds. While the HI titers appeared to be slightly higher after the third immunization (bleed 3) in mice immunized with 2.5 and 5 µg/dose, this difference is considered to be within the assay variation and therefore is not significant. Furthermore, there did not appear to be a dose response in the HI titers generated with increasing amounts of PlyD1. The results are shown in Table 10.

TABLE 10

Hemolysis Inhibition Titers in Sera of Mice Immunized with PlyD1 at Different Doses

| Immunogen | HI Titer* | | | | Fold Increase Between Prebleed to Bleed 3 HI Titer |
|---|---|---|---|---|---|
| | Prebleed | Bleed 1 | Bleed 2 | Bleed 3 | |
| PlyD1 (25 µg) | 4 | 8 | 32 | 64 | 16 |
| PlyD1 (10 µg) | 4 | 8 | 32 | 64 | 16 |
| PlyD1 (5 µg) | 2 | 8 | 64 | 128 | 64 |
| PlyD1 (2.5 µg) | 2 | 8 | 32 | 128 | 64 |
| PlyD1 (1 µg) | 2 | 4 | 32 | 64 | 32 |
| PlyD1 (0.5 µg) | 2 | 8 | 64 | 64 | 32 |

TABLE 10-continued

Hemolysis Inhibition Titers in Sera of Mice Immunized with PlyD1 at Different Doses

| | HI Titer* | | | | Fold Increase Between Prebleed to |
|---|---|---|---|---|---|
| Immunogen | Prebleed | Bleed 1 | Bleed 2 | Bleed 3 | Bleed 3 HI Titer |
| PlyD1 (0.25 µg) | 2 | 4 | 64 | 64 | 32 |
| Placebo (AlOOH) | 2 | 2 | 2 | 2 | 1 |

*HI Titer: highest serum dilution able to completely inhibit hemolysis of a given quantity of recombinant wtPLY. The lower limit of detection of the assay is 4; titers lower than 4 are listed as 2 for statistical purposes.

Antibody titers from the second bleed and third bleed were measured using quantitative anti-PLY ELISA. All PlyD1 immunized mice were able to mount an antibody response to PLY following bleed 2 and bleed 3. There were no significant differences (<2 fold differences) observed between groups immunized with increasing doses of PlyD1, suggesting that all doses tested were still generating saturating amounts of anti-PLY antibodies. ELISA results from the third bleed are shown in Table 11.

TABLE 11

PLY-Specific Antibody Titers for Groups of Mice Immunized with Placebo or Increasing Amount of PlyD1

| Group | Bleed[1] | ELISA Mean Titer |
|---|---|---|
| PlyD1-adjuvanted (25 µg) | Pre-immunization | <3 |
| | Post 3$^{rd}$ immunization | 35724 |
| PlyD1-adjuvanted (10 µg) | Pre-immunization | <3 |
| | Post 3$^{rd}$ immunization | 28900 |
| PlyD1-adjuvanted (5 µg) | Pre-immunization | <3 |
| | Post 3$^{rd}$ immunization | 58699 |
| PlyD1-adjuvanted (2.5 µg) | Pre-immunization | <3 |
| | Post 3$^{rd}$ immunization | 38093 |
| PlyD1-adjuvanted (1 µg) | Pre-immunization | <3 |
| | Post 3$^{rd}$ immunization | 17765 |
| PlyD1-adjuvanted (0.5 µg) | Pre-immunization | <3 |
| | Post 3$^{rd}$ immunization | 25047 |
| PlyD1-adjuvanted (0.25 µg) | Pre-immunization | <3 |
| | Post 3$^{rd}$ immunization | 20883 |
| Placebo (AlOOH) | Pre-immunization | <3 |
| | Post 3$^{rd}$ immunization | 26 |

[1]Performed by anti-PLY quantitative ELISA

Balb/c mice were also immunized with PlyD1 with or without adjuvant, wtPLY at a dose of 5 or 10 and then challenged with a 5 µg dose of wtPLY. The lungs were then harvested for H&E stain to observe tissue damage caused by wtPLY. Compared to controls (mice immunized with Tris-saline, 15% glycerol), wtPLY typically causes perivascular edema, thickened, disrupted alveolar walls, diminished alveolar space, and fluid and blood infiltration of the alveolar spaces. As shown in FIG. 3, mice immunized with PlyD1, PdB, or wtPLY demonstrated significant protection from lung damage after intranasal challenge with wtPLY. The ability of antisera from these immunized mice to inhibit PLY-mediated hemolysis of sheep red blood cells was tested using the HI assay following the first, second and third bleed. Neutralizing antibody titers were increased following bleed 3 compared to bleed 2. Taken together, PlyD1 immunization can generate antibodies that are directly involved in the neutralization of PLY toxicity in vivo.

Figure 5:
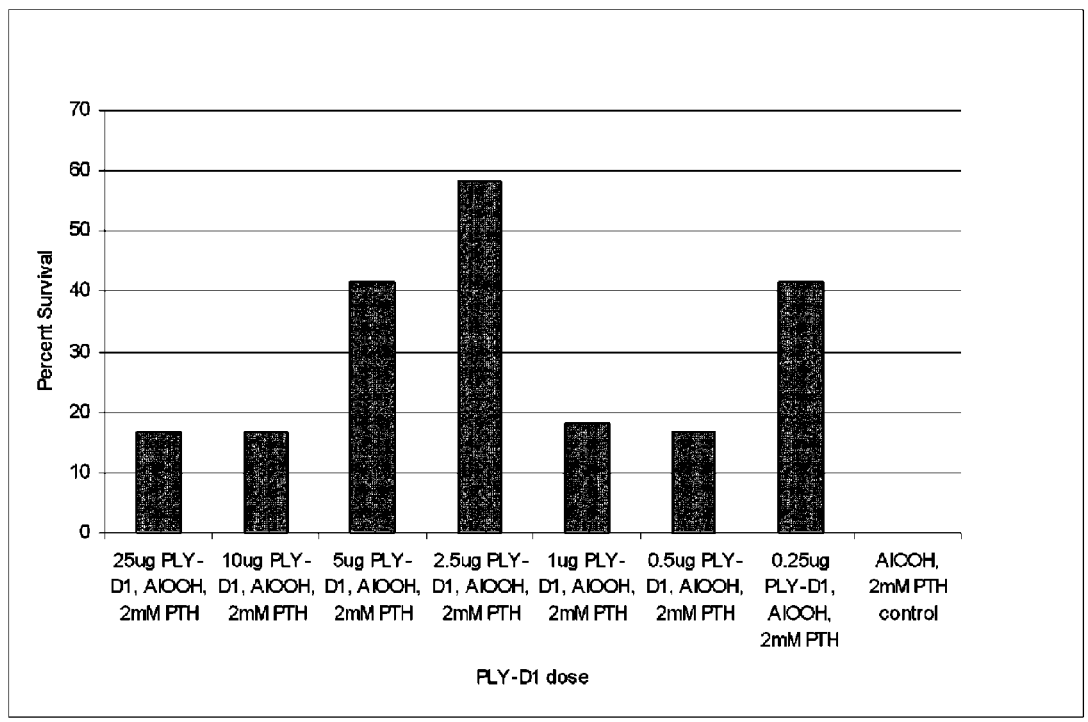
FIG. 5. Survival of CBA/J mice immunized 3× with different doses of Adjuvanted Ply-D1.

CBA/J mice were immunized (I.M) with adjuvant alone (A100H) or with monovalent Ply-D1, 3 times with 3 weeks interval between each immunization. 3 weeks post final immunization, mice were challenged with GT-14453.BM2 (serotype 6B) at $5\times10^5$ CFU/mouse and observed for survival/health for 2 weeks. PlyD1 was formulated as 0.25 µg, 0.5 µg, 1.0 µg, 2.5 µg, 5.0 µg, 10 µg and 25 µg/ml. Data was analyzed by plotting survival/health status of mice and statistically compared using Fisher-one sided test for statistical analysis. As shown in FIG. 5, immunization with recombinant PlyD1 led to protection against lethal challenge in mice.

As shown herein, using the intranasal bacterial challenge model, significant protection was observed in mice immunized with PlyD1 compared to placebo control. PlyD1 mice had significantly lower lung damage when compared to placebo-immunized and PLY challenged mice. Collectively these data indicate that PlyD1 immunization of mice can generate antibodies that are directly involved in the neutralization of PLY toxicity in vivo as well as protect from a lethal IN challenge using live bacteria.

Example 9

Immunogenic Composition and/or Vaccine

The production process for a PlyD1 immunogenic composition and/or vaccine involves: 1) growing recombinant *E. coli* cells that express the PlyD1 protein in a fermenter, using pH-Stat fed batch fermentation; 2) recovering the PlyD1 protein by homogenizing cells followed by 0.2 µm clarification filtration, and concentration by ultrafiltration; 3) purifying the PlyD1 protein using ion-exchange chromatography and hydrophobic interaction chromatography; and, 4) formulating the purified PlyD1 protein with aluminum adjuvant, however other adjuvants known in the art an also be used. These procedures are described herein or well-known to those of skill in the art of vaccine formulation.

PlyD1 may be formulated with an aluminum hydroxide adjuvant in sterile Tris-buffered saline (TBS) without preservative, and prepared as a sterile, white opaque liquid suspension in single-dose vials (containing 0.28 mg of elemental aluminum/dose). Other adjuvants known in the art can also be used to formulate a vaccine. Each 0.5 mL dose of PlyD1 immunogenic composition or vaccine typically contains the following components: recombinant PlyD1 (10 µg (low dose), 25 µg (middle dose), 50 µg (high dose)), and Tris-buffered saline (TBS; 10 mM Tris-HCl pH 7.4, 150 mM sodium chloride), aluminum hydroxide adjuvant (0.28 mg elemental aluminum/dose), and sodium phosphate (2 mM) to optimize binding and stability of adsorbed antigens. The glass vials are filled with 0.72±0.05 mL to give a withdrawable volume of 0.50 mL. An injection (intramuscular, IM) of 0.5 mL from a low dose, middle dose and high dose will give a dosage of either 10 µg, 25 µg or 50 µg of PlyD1, respectively. Each 0.5 mL dose is adjuvanted with 0.28 mg±0.10 mg elemental aluminum. The placebo to be used is TBS. The immunogenic composition or vaccine is typically supplied in 3 mL glass vials that have a 13 mm gray butyl serum stopper that is latex-free and a 13 mm one-piece aluminum seal. The composition is typically a white cloudy suspension and the placebo is a clear solution and must be stored at about 2° C. to 8° C. (e.g., not frozen). The aluminum adjuvant in the product typically settles over time and is re-suspended before use. In preparation for use, the vaccine vial should be inverted about 5 to 10 times until the contents are uniform in appearance. A syringe should be filled immediately after suspension/mixing and the vaccine injected promptly. Routes of administrations may be as described herein, for example, preferably via subcutaneous (SC), intradermal (ID), intramuscular (IM), or oral routes.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. An isolated nucleic acid sequence encoding a wild-type pneumolysin polypeptide comprising an amino acid substitution at threonine 65, glycine 293, and cysteine 428.

2. The isolated nucleic acid sequence of claim 1 wherein the wild-type pneumolysin has at least 90% identity, at least 95% identity, or at least 99% identity to SEQ ID NO:3.

3. The isolated nucleic acid sequence of claim 1 wherein the substitution of threonine 65 is by cysteine.

4. The isolated nucleic acid sequence of claim 1 wherein the substitution is of glycine 293 is by an amino acid selected from the group consisting of cysteine, valine, and threonine.

5. The isolated nucleic acid sequence of claim 1 wherein the substitution of cysteine 428 is by alanine.

6. The isolated nucleic acid sequence of claim 1 wherein the substitution of threonine 65 is by cysteine, the substitution is of glycine 293 is by an amino acid selected from the group consisting of cysteine, valine, and threonine, and the substitution of cysteine 428 is by alanine.

7. The isolated nucleic acid sequence of claim 1 wherein the substitution of threonine 65 is by cysteine, the substitution of glycine 293 is by cysteine and the substitution of cysteine 428 is by alanine.

8. An expression vector comprising the nucleic acid sequence of claim 1.

9. A composition comprising the expression vector of claim 7.

10. A host cell comprising the nucleic acid sequence of claim 1.

11. A host cell comprising the expression vector of claim 1.

12. A method of producing a polypeptide consisting of a wild-type pneumolysin polypeptide comprising an amino acid substitution at threonine 65, glycine 293, and cysteine 428 comprising transfecting a host cell with an expression vector encoding the polypeptide, culturing the host cell such that the polypeptide is expressed, and isolating the polypeptide.

13. The method of claim 12 wherein the wild-type pneumolysin polypeptide has at least 90% identity, at least 95% identity, or at least 99% identity to SEQ ID NO:3.

14. The method of claim 12 wherein the substitution of threonine 65 is by cysteine, the substitution of glycine 293 is by cysteine and the substitution of cysteine 428 is by alanine.

* * * * *